United States Patent
Rice et al.

(10) Patent No.: US 12,082,997 B2
(45) Date of Patent: Sep. 10, 2024

(54) REMOVABLE AND REPLACEABLE DRESSING INTERFACE FOR A NEGATIVE-PRESSURE THERAPY SYSTEM

(71) Applicant: KCI Licensing, Inc., San Antonio, TX (US)

(72) Inventors: Justin Rice, Denver, CO (US); Matthew Francis Cavanaugh, II, San Antonio, TX (US); Christopher Brian Locke, Bournemouth (GB); Christopher Allen Carroll, San Antonio, TX (US); Benjamin Stokes, Ringwood (GB); Benjamin Andrew Pratt, Poole (GB); Thomas Alan Edwards, Hampshire (GB)

(73) Assignee: KCI Licensing, Inc., San Antonio, TX (US)

( * ) Notice: Subject to any disclaimer, the term of this patent is extended or adjusted under 35 U.S.C. 154(b) by 256 days.

(21) Appl. No.: 17/424,282

(22) PCT Filed: Jan. 24, 2020

(86) PCT No.: PCT/US2020/014986
§ 371 (c)(1),
(2) Date: Jul. 20, 2021

(87) PCT Pub. No.: WO2020/159823
PCT Pub. Date: Aug. 6, 2020

(65) Prior Publication Data
US 2022/0088286 A1    Mar. 24, 2022

Related U.S. Application Data

(60) Provisional application No. 62/798,275, filed on Jan. 29, 2019.

(51) Int. Cl.
*A61F 13/05* (2024.01)
*A61F 13/02* (2024.01)
(Continued)

(52) U.S. Cl.
CPC .......... *A61F 13/05* (2024.01); *A61F 13/0253* (2013.01); *A61F 13/0263* (2013.01);
(Continued)

(58) Field of Classification Search
CPC ............ A61F 13/00068; A61F 13/0216; A61F 13/0253; A61F 13/0259; A61F 13/0263;
(Continued)

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Leslie A Lopez
*Assistant Examiner* — Timothy L Flynn

(57) ABSTRACT

A dressing interface for connecting a negative-pressure source to a dressing may have a coupling member comprising an aperture, a first adhesive region having a first region peel strength, and a second adhesive region having a second region peel strength less than the first region peel strength.

(Continued)

The dressing interface may further have a flange coupled to the coupling member, and a conduit housing coupled to the flange and extending through the aperture in the contact layer.

14 Claims, 15 Drawing Sheets

(51) Int. Cl.
  *A61F 13/0246* (2024.01)
  *A61M 1/00* (2006.01)
(52) U.S. Cl.
  CPC .............. *A61M 1/90* (2021.05); *A61M 1/912* (2021.05); *A61M 1/915* (2021.05); *A61M 1/772* (2021.05)
(58) Field of Classification Search
  CPC ........ A61F 13/0246; A61F 2013/00561; A61F 2013/00804; A61F 2013/00838; A61F 5/443; A61M 1/77; A61M 1/772; A61M 1/90; A61M 1/91; A61M 1/913; A61M 1/916; A61M 1/917; A61M 1/918; A61M 1/92; A61M 1/94; A61M 1/95; A61M 1/96; A61M 1/962; A61M 1/984
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0138602 A1* | 7/2004 | Rossen ............... A61F 13/0226 602/41 |

(56) References Cited

U.S. PATENT DOCUMENTS

| | | | |
|---|---|---|---|
| 2009/0227969 A1* | 9/2009 | Jaeb | A61F 13/00068 604/313 |
| 2009/0234309 A1* | 9/2009 | Vitaris | A61M 1/915 602/57 |
| 2014/0039426 A1* | 2/2014 | Coulthard | A61F 13/00055 29/601 |
| 2014/0046278 A1 | 2/2014 | Eckstein et al. | |
| 2014/0163491 A1 | 6/2014 | Schuessler et al. | |
| 2015/0057625 A1 | 2/2015 | Coulthard | |
| 2015/0080788 A1 | 3/2015 | Blott et al. | |
| 2017/0189236 A1* | 7/2017 | Locke | A61F 13/01029 |
| 2017/0189237 A1 | 7/2017 | Locke et al. | |
| 2019/0091072 A1 | 3/2019 | Hu et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102014227042 A1 | 6/2016 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| NO | 90/010424 A1 | 9/1990 |
| SG | 71559 | 4/2002 |
| WO | 80/02182 A1 | 10/1980 |
| WO | 87/04626 A1 | 8/1987 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2011090986 A2 | 7/2011 |
| WO | 2015065615 A1 | 5/2015 |
| WO | 2017048866 A1 | 3/2017 |
| WO | 2018081217 A1 | 5/2018 |
| WO | 2018226624 A1 | 12/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for Corresponding Application No. PCT/US2020/014986, mailed Jul. 8, 2020.

\* cited by examiner

REMOVABLE AND REPLACEABLE DRESSING INTERFACE FOR A NEGATIVE-PRESSURE THERAPY SYSTEM

RELATED APPLICATION

The present invention claims the benefit of the filing of U.S. Provisional Patent Application No. 62/798,275, filed Jan. 29, 2019, which is incorporated herein by reference for all purposes.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a removable and replaceable dressing interface for connecting a negative-pressure source to a dressing may comprise or consist essentially of a primary cover contact layer, a secondary cover contact layer, and a negative-pressure adapter. The primary cover contact layer may be a low-tack gel adhesive, such as, for example, a silicone adhesive with a peel strength of about 0.8 N. However, in some embodiments for example, the primary cover contact layer may be formed of a hydrocolloid adhesive or low-tack polyurethane (PU) gel adhesive. In some embodiments, the primary drape contact layer may be perforated to aid in sufficiently sealing the negative-pressure adapter to the cover when in normal use by a patient. The perforations may have two sizes which allow for protrusion of the secondary drape contact layer through the primary cover contact layer to the cover of the dressing. The secondary cover contact layer may be a high-tack, adhesive-coated polyurethane film. The two perforation sizes in the primary cover contact layer may allow for variation in the removal peel force when the dressing interface is adhered to the cover of the dressing. The portion of the dressing interface with the larger perforations allows more of the high-tack secondary cover contact layer to adhere to the cover, and thus may act as an anchor to the dressing interface. This portion may require the greatest peel force to remove the dressing interface from the cover. The portion of the dressing interface with the smaller perforations allows less of the high-tack secondary cover contact layer to adhere to the cover. This portion may require a lesser peel force to remove the dressing interface from the cover. Accordingly, this portion with the smaller perforations may have a peel force that allows a user to remove and re-apply the dressing interface to the cover while still maintaining a sufficient seal to deliver negative-pressure therapy to a tissue site. The peel force of the portion of the dressing interface having the smaller perforations may be low enough to allow the dressing interface to be removed without damaging or destroying the cover. Additionally, the negative-pressure port may have a flat or straight portion which may allow the negative-pressure port to hinge when the dressing interface is removed or peeled up from the cover.

More generally, some embodiments may comprise a dressing interface for connecting a negative-pressure source to a dressing, the dressing interface having a coupling member comprising an aperture, a first adhesive region having a first region peel strength, and a second adhesive region having a second region peel strength less than the first region peel strength. The dressing interface may further include a negative-pressure port for the delivery of negative pressure, wherein the negative-pressure port is coupled to the coupling member.

In some embodiments, the negative-pressure port includes a flange and a conduit housing coupled to the flange and extending through the aperture in the contact layer.

In some embodiments, the coupling member may further comprise a shell layer and a contact layer comprising a plurality of apertures, wherein the shell layer is configured to extend at least partially through the plurality of apertures in the contact layer. In some embodiments, the plurality of apertures further comprises a first plurality of apertures and a second plurality of apertures.

In some embodiments, the second adhesive region is configured to be removable from a cover without destruction of the cover, while the first adhesive region is configured to remain adhered to the cover.

Alternatively, other example embodiments may comprise a dressing interface for connecting a negative-pressure source to a dressing, the dressing interface having a base, a conduit housing attached to the base, a first layer coupled to the base, and a second layer. The first layer includes an adhesive with a first peel strength and an aperture through which the conduit housing is configured to pass. The second layer has an adhesive with a second peel strength less than the first peel strength of the first layer, a first plurality of apertures, and a second plurality of apertures. The first layer is configured to extend at least partially through the first and second plurality of apertures in the second layer.

In some embodiments, a first portion of the first layer is configured to extend through the first plurality of apertures and cooperate with the second layer to form a first adhesive region having a first region peel strength, and a second portion of the first layer is configured to extend through the second plurality of apertures and cooperate with the second layer to form a second adhesive region having a second region peel strength less than the first region peel strength.

In other example embodiments, a dressing interface for connecting a negative-pressure source to a dressing may comprise a negative-pressure port coupled to at least one of a first layer and a second layer. The first layer may have a first side, a second side, and an adhesive on the first side having a first peel strength. The second layer may have a first side, a second side coupled to the first side of the first layer, the second layer comprising an adhesive having a second peel strength less than the first peel strength of the first layer, and a plurality of apertures. The first layer is configured to extend at least partially through the plurality of apertures in the second layer.

In yet other example embodiments, a dressing interface for connecting a negative-pressure source to a dressing may comprise a base, a conduit housing attached to the base, a shell layer having a first side, a second side, and an aperture through which the conduit housing is configured to pass, the shell layer coupled to the base, and a contact layer having a first side, a second side coupled to the first side of the shell layer, and an aperture in which the base is configured to reside.

In yet other example embodiments, a dressing interface for connecting a negative-pressure source to a dressing may comprise a stretch releasing adhesive layer having an adhesive portion, a tab, and an aperture, a flange coupled to the stretch releasing adhesive layer, and a conduit housing coupled to the flange and extending through the aperture in the stretch releasing adhesive layer.

In yet other example embodiments, a dressing interface for connecting a negative-pressure source to a dressing may comprise a coupling member comprising an aperture, a first adhesive region having a first region peel strength, a second adhesive region having a second region peel strength less than the first region peel strength, and a hinge line between the first adhesive region and the second adhesive region.

In some embodiments, the dressing interface may additionally include a fluid conductor comprising an applicator and a bridge, wherein the applicator is coupled to the coupling member.

A system for treating a tissue site is also described herein, wherein some example embodiments include a manifold for disposing proximate the tissue site, a cover for placement on a patient's epidermis and configured to form a fluid seal over the manifold, the dressing interface as described for coupling to the cover, and a negative-pressure source for coupling to the manifold via the dressing interface.

Additionally, a method of treating a tissue site with negative pressure may comprise applying a manifold to the tissue site, applying a cover on the patient's epidermis to form a fluid seal over the manifold, applying the dressing interface as described to a first location on the cover, fluidly coupling the manifold to a negative-pressure source, and applying negative pressure from the negative-pressure source to the manifold and promoting healing and tissue granulation.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
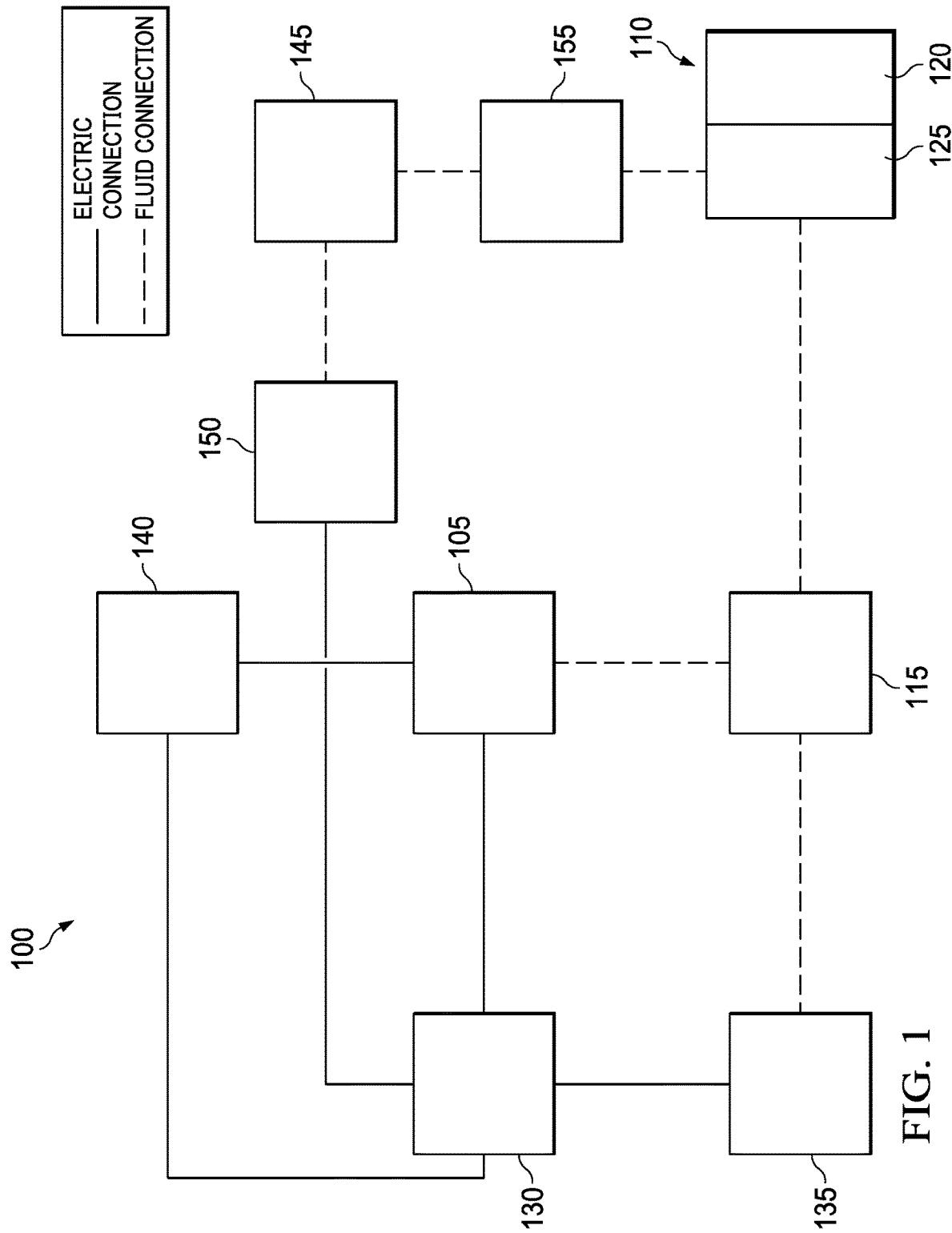
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours ($g/m^2/24$ hours) in some embodiments, measured using an upright cup technique according to ASTM E96/E96M Upright Cup Method at 38° C. and 10% relative humidity (RH). In some embodiments, an MVTR up to 5,000 $g/m^2/24$ hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis, Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of −135 mmHg for a specified period of time (e.g., 5 min), followed by a specified period of time (e.g., 2 min) of deactivation. The cycle can be repeated by activating the negative-pressure source 105 which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

The controller 130 may also control the fluid dynamics of instillation by providing a continuous flow of solution or an intermittent flow of solution. Negative pressure may be applied to provide either continuous flow or intermittent flow of solution. The application of negative pressure may be implemented to provide a continuous pressure mode of operation to achieve a continuous flow rate of instillation solution through the tissue interface 120, or it may be implemented to provide a dynamic pressure mode of operation to vary the flow rate of instillation solution through the tissue interface 120. Alternatively, the application of negative pressure may be implemented to provide an intermittent mode of operation to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied. The controller 130 may be utilized to select a mode of operation and the duration of the negative pressure treatment before commencing another instillation cycle by instilling more solution.

Figure 2:
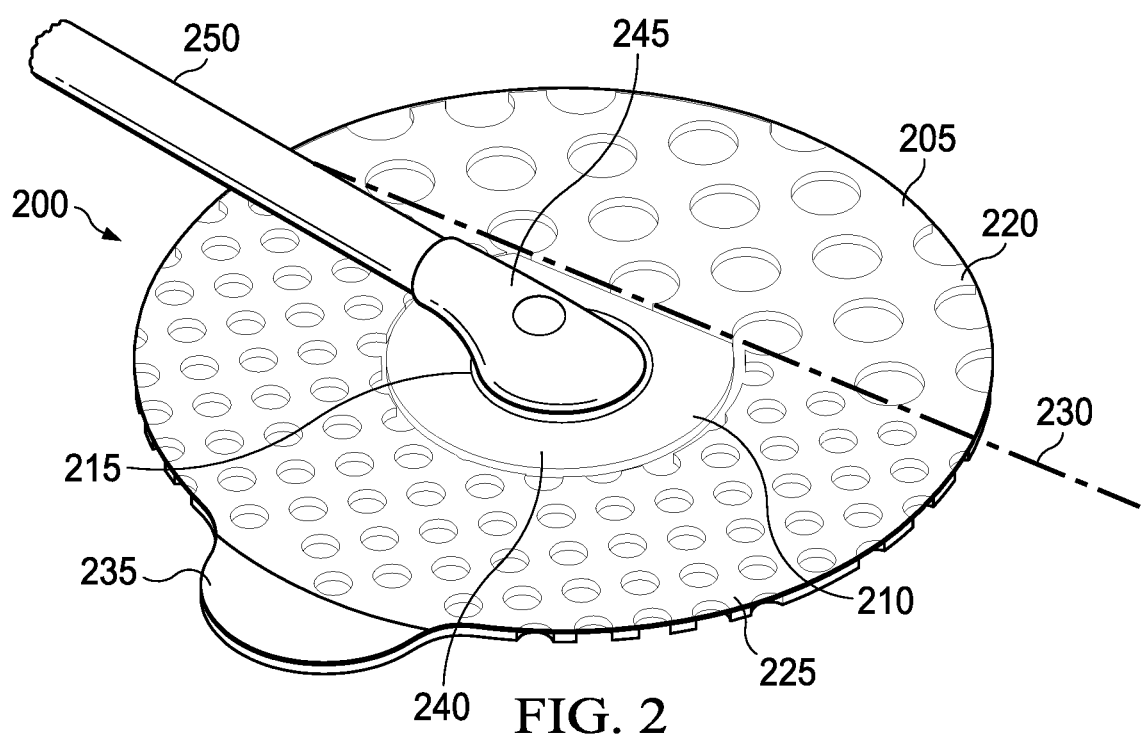
FIG. 2 is an isometric view of an example of a dressing interface, illustrating additional details that may be associated with some example embodiments of the therapy system of FIG. 1.

FIG. 2 is an isometric view illustrating a dressing interface 200 configured to connect the negative-pressure source 105 to the dressing 110. The dressing interface 200 may be easily removed, replaced, and/or repositioned on the cover 125 without damaging or destroying the cover 125. In the example of FIG. 2, the dressing interface 200 comprises a coupling member 205 coupled to a negative-pressure port 210. The coupling member 205 includes an aperture 215, a first adhesive region 220, and a second adhesive region 225.

A hinge line 230 may be formed between the first adhesive region 220 and the second adhesive region 225. The first adhesive region 220 has a first peel strength and the second adhesive region 225 has a second peel strength, wherein the second peel strength is less than the first peel strength. The dressing interface 200 may further include a tab 235 coupled to the second adhesive region 225.

The negative-pressure port 210 includes a base, such as a flange 240, and a conduit housing 245 extending from the flange 240. The conduit housing 245 may be an elbow connector. The conduit housing may extend through the aperture 215 in the coupling member 205. A fluid conductor 250, which may be a flexible tube, for example, may be fluidly coupled on one end to the conduit housing 245.

Figure 3:
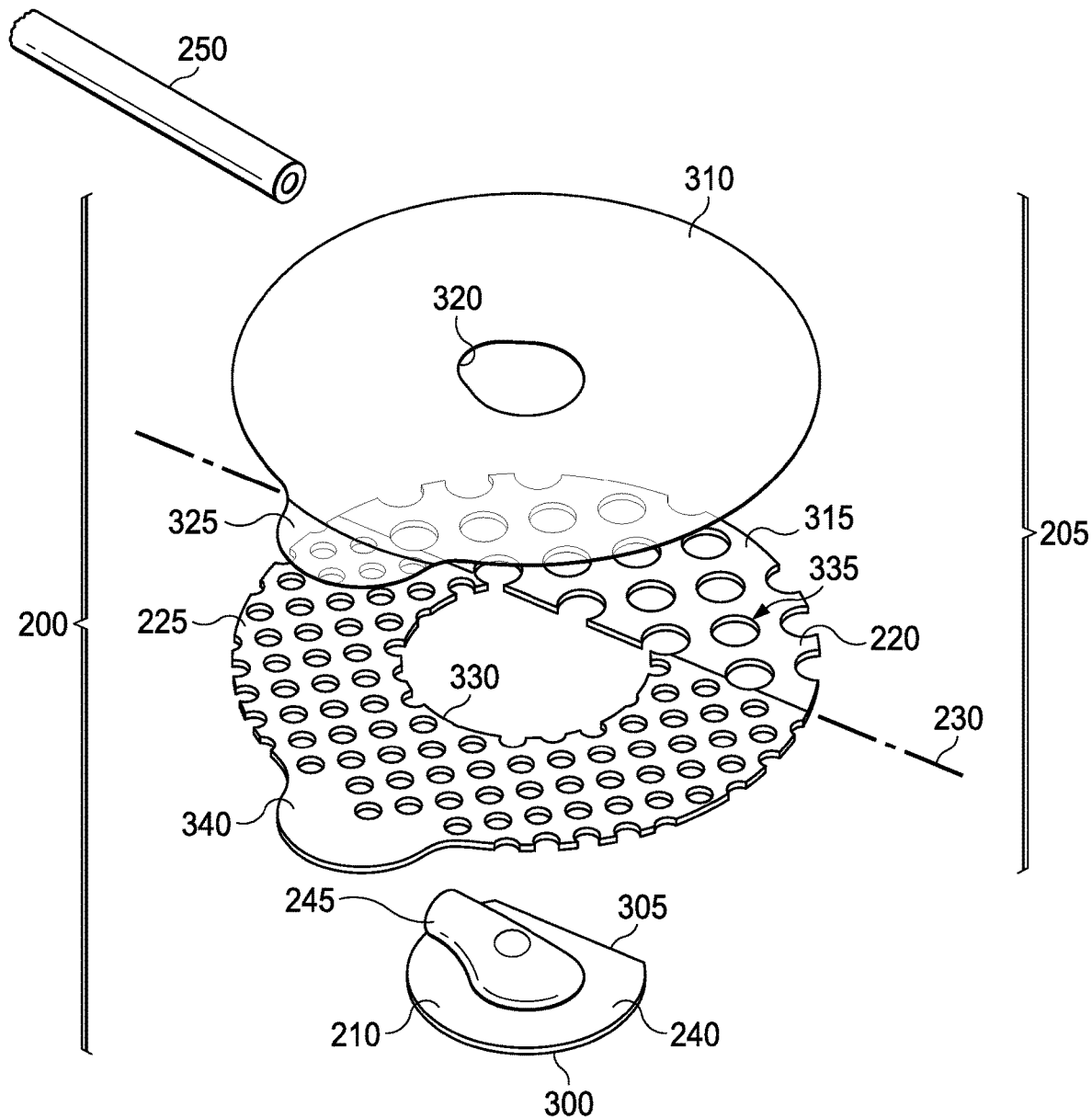
FIG. 3 is an exploded view of the dressing interface of FIG. 2.

FIG. 3 is an exploded view of the dressing interface 200 of FIG. 2, illustrating additional details that may be associated with certain embodiments. The flange 240 of the negative-pressure port 210 may have at least one straight edge and one rounded edge. For example, the flange 240 may have a rounded edge 300 corresponding to a major arc of a circle, and a straight edge 305 corresponding to a chord of the circle. The rounded edge 300 and the straight edge 305 define a shape corresponding to a major segment of the circle. That is, the flange 240 may have straight section or flat spot. In some embodiments, the straight edge 305 may be parallel to the hinge line 230. In some examples, the straight edge 305 may be offset from the hinge line 230 a distance into or toward the second adhesive region 225. In other embodiments, the straight edge 305 may be collinear with the hinge line 230. The straight edge 305 may lie along the hinge line 230 without any offset from the hinge line 230. The straight edge 305 in the flange 240 can allow the negative-pressure port 210 to hinge about the hinge line 230 if the second adhesive region 225 is removed from the cover 125 as described herein. In some embodiments, the flange 240 of the negative-pressure port 210 may be flexible enough to permit folding and bending of the flange 240 such that a portion of the flange 240 may extend across the hinge line 230 and not impede or prohibit the hinging of the second adhesive region 225.

Although the flange 240 is described as being having a truncated circular shape, in some embodiments, the flange 240 may have any suitable shape, such as, for example, circles, triangles, squares, rectangles, pentagons, hexagons, octagons, stars, ovals, polygons, or rectilinear shapes. In some embodiments where the flange 240 has a shape with at least one straight edge (e.g., triangle, square, rectangle, pentagon, hexagon, octagon), the straight edge may be parallel to or collinear with the hinge line 230 as described above with respect to the straight edge 305.

With continued reference to FIG. 3, the coupling member 205 may include a shell layer 310 and a contact layer 315. The shell layer 310 may be formed from any material that allows for a fluid seal. A fluid seal is a seal adequate to maintain negative pressure at a desired site given the particular negative-pressure source or system involved. The shell layer 310 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 or 2317 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, California; polyether block polyamide copolymer (PEBAX), for example, from Arkema, France; Expopack 2327; or other appropriate material.

The shell layer 310 may be vapor permeable and liquid impermeable. In some embodiments, the shell layer 310 may be a flexible, breathable film, membrane, or sheet having a high MVTR of, for example, at least about 300 g/m$^2$ per 24 hours. In other embodiments, a low or no vapor transfer film might be used. The shell layer 310 may comprise a range of medically suitable films having a thickness between about 15 microns (μm) to about 50 microns (μm). In some embodiments, the shell layer 310 may be formed of the same material as the cover 125. In some embodiments, the shell layer 310 may be clear, transparent, translucent, opaque and/or colored.

The shell layer 310 may have a first side and a second side. The first side of the shell layer 310 may comprise an adhesive. The adhesive may be coupled to the first side of the shell layer 310. In some embodiments, the adhesive may be coated or deposited on the first side of the shell layer 310. The adhesive may be a medically-acceptable adhesive. The adhesive may also be flowable. For example, the adhesive may comprise an acrylic adhesive, rubber adhesive, high-tack or tacky silicone adhesive, polyurethane, or other adhesive substance. In some embodiments, the adhesive of the shell layer 310 may be a pressure-sensitive adhesive, such as an acrylic adhesive with coating weight of 15 grams/m$^2$ (gsm) to 70 grams/m$^2$ (gsm). In some embodiments, the adhesive may have a peel strength or resistance to being peeled from a stainless steel material in a range of about 6.4N to about 8.8 N. In some embodiments, the adhesive may have a peel strength or resistance to being peeled from a stainless steel material of about 7.8 N. The peel strength may be measured by applying a 1 inch (2.54 cm) wide test strip of the adhesive to a stainless steel plate using a roller. The test strip is then peeled back over itself (at an angle of 180 degrees) and the force required to peel the test strip is measured. The test is conducted at on a stainless steel substrate at 23 degrees C. at 50% relative humidity based on ASTM D3330. In some embodiments, the adhesive of the shell layer 310 may be reduced or deactivated using ultraviolet light. Ultraviolet light may be shined upon the shell layer 310 and the ultraviolet light may reduce the peel strength of the adhesive a sufficient amount to allow removal of the dressing interface 200 from the cover 125 without damage to or destruction of the cover 125.

The shell layer 310 further includes an aperture 320. In some embodiments, the aperture 320 may be centrally located in the shell layer 310. The aperture 320 may be sized or dimensioned to receive the conduit housing 245 of the negative-pressure port 210. In some embodiments, the shape of the aperture 320 may be coextensive or congruent with the shape of the conduit housing 245 where the conduit housing 245 meets the flange 240. In other embodiments, the size of the aperture 320 in the shell layer 310 may be larger than the size of the conduit housing 245 where the conduit housing 245 meets the flange 240. In some embodiments, the shape of the aperture 320 may be different from the shape of the conduit housing 245 where the conduit housing 245 meets the flange 240. The top side of the flange 240 of the negative-pressure port 210 may be coupled to the first side of the shell layer 310 by the adhesive on the first side of the shell layer 310 to create a fluid seal around the flange 240. In some embodiments, the shell layer 310 may also include a tab 325 located on the periphery of the shell layer 310 on the second adhesive region 225 side of the hinge line 230.

In some embodiments, the contact layer 315 may have a first side and a second side. The second side of the contact layer 315 may be coupled to the first side of the shell layer 310. The contact layer 315 may comprise an adhesive. For example, the contact layer 315 may be a soft, pliable material suitable for providing a fluid seal with the cover 125 as described herein. For example, the contact layer 315 may comprise a silicone gel, a soft silicone, hydrocolloid, hydrogel, polyurethane gel, polyolefin gel, hydrogenated styrenic copolymer gels, a foamed gel, a soft closed-cell foam such as polyurethanes and polyolefins coated with an adhesive, polyurethane, polyolefin, hydrogenated styrenic copolymers, or a film, membrane, or sheet coated with an adhesive. The contact layer 315 may be comprised of hydrophobic or hydrophilic materials. In some embodiments, the contact layer 315 may be clear, transparent, translucent, opaque and/or colored. The contact layer 315 may have a thickness between about 500 microns (μm) and about 1000 microns (μm). In some embodiments, the contact layer 315 has a stiffness between about 5 Shore 00 and about 80 Shore 00. In some embodiments, the contact layer 315 has a peel strength in a range of about 0.37 N to about 0.44 N. In some embodiments, for example, the contact layer 315 has a peel strength in a range of about 0.5 N to about 1.0 N. In some embodiments, for example, the contact layer 315 has a peel strength of about 0.4 N. In some embodiments, for example, the contact layer 315 has a peel strength of about 0.8 N. In some embodiments, for example, the contact layer 315 has a peel strength of about 0.9 N. In some embodiments, for example, the contact layer 315 has a peel strength of about 2.8 N. The peel strength of the contact layer 315 may be less than the peel strength of the adhesive of the shell layer 310.

In some embodiments, the ratio of the peel strength of the contact layer 315 to the peel strength of the adhesive of the shell layer 310 may be about 1:2. In some embodiments, the ratio of the peel strength of the contact layer 315 to the peel strength of the adhesive of the shell layer 310 may be about 1:2.3. In some embodiments, the ratio of the peel strength of the contact layer 315 to the peel strength of the adhesive of the shell layer 310 may be about 1:3.1. In some embodiments, the ratio of the peel strength of the contact layer 315 to the peel strength of the adhesive of the shell layer 310 may be about 1:7.1. In some embodiments, the ratio of the peel strength of the contact layer 315 to the peel strength of the adhesive of the shell layer 310 may be about 1:8. In some embodiments, the ratio of the peel strength of the contact layer 315 to the peel strength of the adhesive of the shell layer 310 may be about 1:9.8. In some embodiments, the ratio of the peel strength of the contact layer 315 to the peel strength of the adhesive of the shell layer 310 may be about 1:11. In some embodiments, the ratio of the peel strength of the contact layer 315 to the peel strength of the adhesive of the shell layer 310 may be about 1:14.5. In some embodiments, the ratio of the peel strength of the contact layer 315 to the peel strength of the adhesive of the shell layer 310 may be about 1:17.3. In some embodiments, ratio of the peel strength of the contact layer 315 to the peel strength of the adhesive of the shell layer 310 may be about 1:19.5. In some embodiments, the ratio of the peel strength of the contact layer 315 to the peel strength of the adhesive of the shell layer 310 may be about 1:20. In some embodiments, the ratio of the peel strength of the contact layer 315 to the peel strength of the adhesive of the shell layer 310 may be about 1:23.8. In some embodiments, the ratio of the peel strength of the contact layer 315 to the peel strength of the adhesive of the shell layer 310 may range from about 1:2 to about 1:23.8. In some embodiments, the ratio of the peel strength of the contact layer 315 to the peel strength of the adhesive of the shell layer 310 may range from about 1:2 to about 1:25.

The contact layer 315 may further include an aperture 330 located in the second adhesive region 225. The aperture 330 may be sized or dimensioned to receive the flange 240 of the negative-pressure port 210 therein. In some embodiments, the shape of the aperture 330 may be coextensive or congruent with the shape of the flange 240 of the negative-pressure port 210. In embodiments where flange 240 is a truncated circle having the straight edge 305, the aperture 330 may also have a truncated circle shape that corresponds to the shape of the flange 240. In some embodiments, the aperture 330 may be located such that the straight edge 305 of the flange 240 may be parallel to the hinge line 230 in the coupling member 205. For example, the straight edge 305 may be parallel to the hinge line 230, but may be offset from the hinge line 230 a distance into or toward the second adhesive region 225. In other embodiments, the straight edge 305 may be collinear with the hinge line 230. The straight edge 305 may lie along the hinge line 230 without any offset from the hinge line 230. In some embodiments, the flange 240 of the negative-pressure port 210 has a thickness and the contact layer 315 has a thickness at least as thick as the thickness of the flange 240. In other embodiments, the thickness of the contact layer 315 is less than the thickness of the flange 240. Thus, the flange 240 may be thicker than the contact layer 315.

The contact layer 315 may further include a plurality of apertures 335. The plurality of apertures 335 may be formed by cutting, perforating, punching, or by other suitable techniques for forming an aperture, opening, perforation, or hole in the contact layer 315, including but not limited to using a single- or multiple-blade cutter, a laser, a water jet, a hot knife, a computer numeric control (CNC) cutter, a hot wire, local RF or ultrasonic energy, and/or a single- or multiple-punch tool. The plurality of apertures 335 in the contact layer 315 may have many shapes including but not limited to, circles, triangles, rectangles, squares, pentagons, hexagons, octagons, ovals, ellipses, stars, polygons, slits, complex curves, and rectilinear shapes or may have some combination of shapes.

The contact layer 315 may further include a tab 340 located on the periphery of the contact layer 315 on the second adhesive region 225 side of the hinge line 230. The tab 340 of the contact layer 315 and the tab 325 of the shell layer 310 may cooperate to form tab 235 of coupling member 205.

Figure 4:
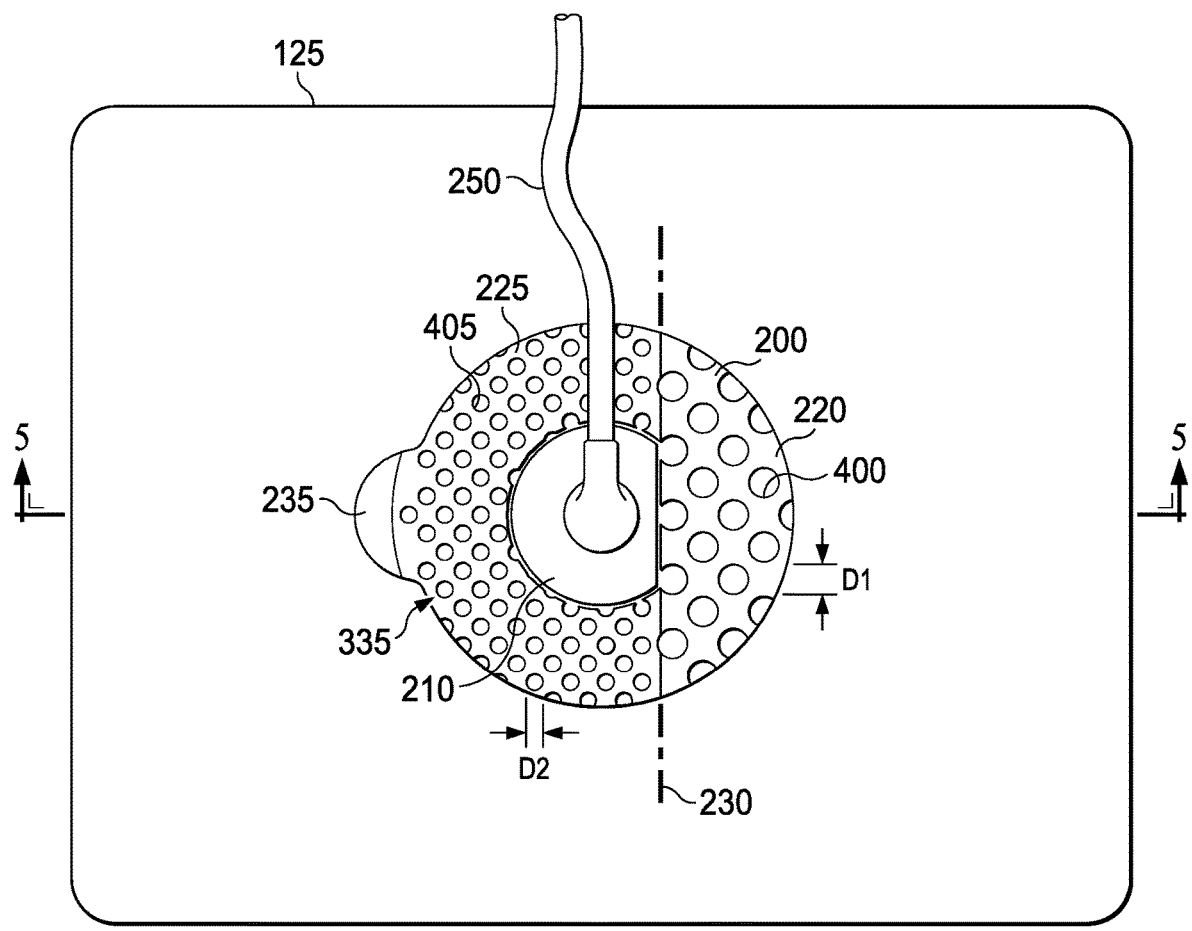
FIG. 4 is a top view of the dressing interface of FIG. 2 as assembled and coupled to an example of a cover that may be associated with some example embodiments of the therapy system of FIG. 1.

FIG. 4 illustrates a top view of the dressing interface 200 as assembled and coupled to a cover 125. As shown in FIG. 4, the plurality of apertures 335 may include a first plurality of apertures 400 and a second plurality of apertures 405. At least one of the first plurality of apertures 400 is located on a first side of the hinge line 230 (e.g., in the first adhesive region 220) and at least one of the second plurality of apertures 405 is located on a second side of the hinge line 230 opposite the first side (e.g., in the second adhesive region 225). In some embodiments, the first plurality of apertures 400 and the second plurality of apertures 405 in the contact layer 315 may be substantially circular in shape. The width of each of the first plurality of apertures 400 and the second plurality of apertures 405 may define the area of each of the first plurality of apertures 400 and the second plurality of apertures 405. As shown in the example of FIG. 4 where the plurality of apertures 405 are circular, the diameter D1, and thus the open area, of each of the first plurality of apertures 400 is larger than the diameter D2 and open area of each of the second plurality of apertures 405. For example, in some embodiments, the diameter D1 of the first plurality of apertures 400 may be in a range of about 4 millimeters to about 15 millimeters. In some embodiments, the diameter D1 of the first plurality of apertures 400 may be in a range of about 5 millimeters to about 10 millimeters. In some embodiments, the diameter D1 of the first plurality of apertures 400 may be about 10 millimeters. For example, in some embodiments, the diameter D2 of the second plurality of apertures 405 may be in a range of about 1 millimeters to about 10 millimeters. In some embodiments, the diameter D2 of the second plurality of apertures 405 may be in a range of about 2 millimeters to about 7 millimeters. In some embodiments, the diameter D2 of the second plurality of apertures 405 may be about 5 millimeters.

Although each aperture of the first plurality of apertures 400 is shown as having the same diameter D1 and each aperture of the second plurality of apertures 405 as having the same diameter D2, it will be understood that in other embodiments, the apertures of the first plurality of apertures 400 may have differing dimensions (and thus open areas) and the apertures of the second plurality of apertures 405 may have differing dimensions (and thus open areas). For example, the first plurality of apertures 400 may have apertures of two or more open areas which cooperate to form an overall open area of the first adhesive region 220. Likewise, the second plurality of apertures 405 may have apertures of two or more open areas which cooperate to form an overall open area of the second adhesive region 225. Therefore, much like the differing diameters of dimples on a golf ball, in some embodiments, the dimensions of the apertures in first plurality of apertures 400 may vary and the dimensions of the apertures in the second plurality of apertures 405 may vary.

The first plurality of apertures 400 are shown as having a circular shape; however, in other embodiments the first plurality of apertures 400 may have many shapes including but not limited to, triangles, rectangles, squares, pentagons, hexagons, octagons, ovals, ellipses, stars, polygons, slits, complex curves, rectilinear shapes or may have some combination of shapes. Additionally, the second plurality of apertures 405 are shown as having a circular shape; however, in other embodiments the second plurality of apertures 405 may have many shapes including but not limited to, triangles, rectangles, squares, pentagons, hexagons, octagons, ovals, ellipses, stars, polygons, slits, complex curves, rectilinear shapes or may have some combination of shapes.

Figure 5:
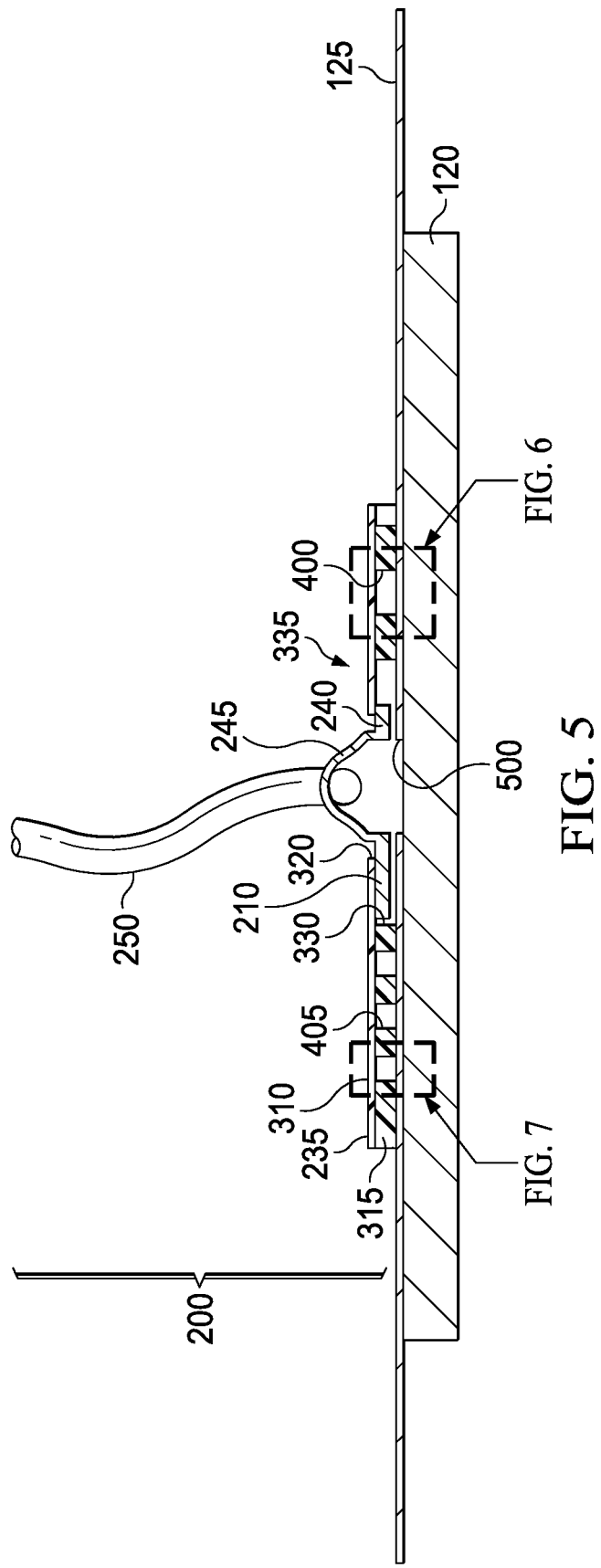
FIG. 5 is a cross-section view of the dressing interface and cover of FIG. 4, and an example of a tissue interface that may be associated with some example embodiments of the therapy system of FIG. 1.

FIG. 5 is a cross-section of the dressing interface 200 of FIG. 4 taken along section line 5-5, illustration additional details that may be associated with some embodiments. For example, when the dressing interface 200 is assembled, the flange 240 of the negative-pressure port 210 may be located below shell layer 310 and the conduit housing 245 may extend upward through the aperture 320 in shell layer 310. The second side of the contact layer 315 may be coupled to the first side of the shell layer 310 by the adhesive on the first side of the shell layer 310. Additionally, the flange 240 of the negative-pressure port 210 may be located in the aperture 330 of the contact layer 315. The aperture 320 in the shell layer 310 and the aperture 330 in the contact layer 315 may cooperate to form the aperture 215 in coupling member 205. As further shown in FIG. 5, the dressing interface 200 may then be placed on top of the cover 125 so that the conduit housing 240 of the negative-pressure port 210 is located over an aperture 500 in the cover 125 and so that the fluid conductor 250 may be fluidly coupled with the tissue interface 120 through the aperture 500. In other embodiments, for example, the flange 240 of the negative-pressure port 210 may be located above shell layer 310. For example, the bottom side of the flange 240 may be adhered to the second side or top side of shell layer 310 to create a fluid seal.

Figure 6:
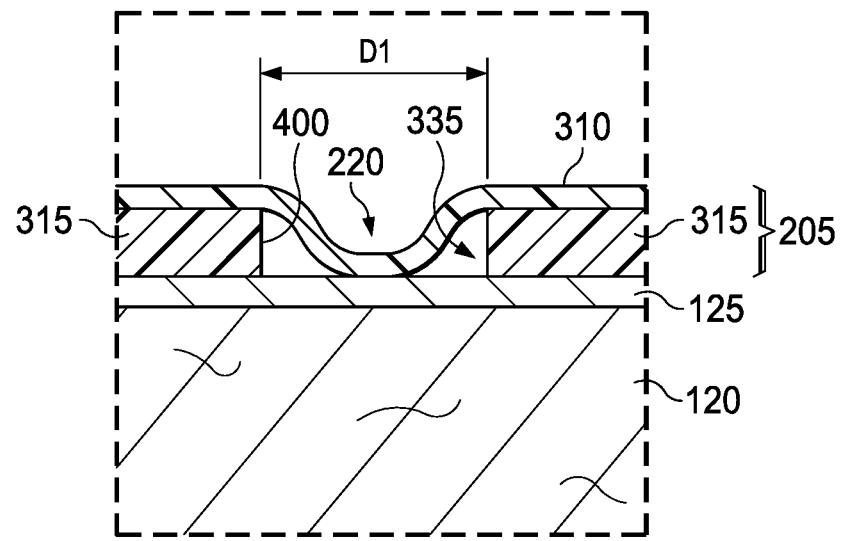
FIG. 6 and FIG. 7 are detail views of the dressing interface, cover, and tissue interface of FIG. 5.
Figure 7:
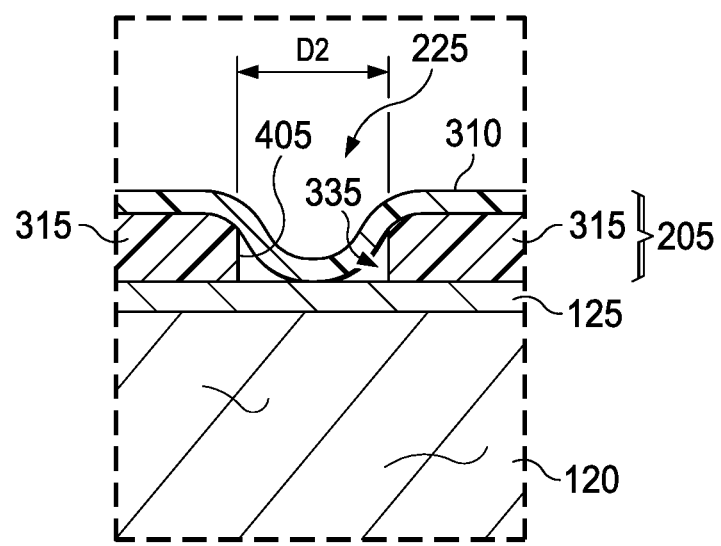

FIG. 6 and FIG. 7 are detail views of features in the example of FIG. 5. In FIG. 6 and FIG. 7, the shell layer 310 may extend or be pressed through the plurality of apertures 335 to contact the cover 125 for securing the dressing interface 200 to, for example, the cover 125. The plurality of apertures 335 may provide sufficient contact of the shell layer 310 to the cover 125 to secure the dressing interface 200 to the cover 125. The plurality of apertures 335 may be sized to control the amount of the shell layer 275 extending through the plurality of apertures 335 in the contact layer 315 to reach the cover 125. Accordingly, the configuration of the plurality of apertures 335, the shell layer 310 and the contact layer 315, may permit release and repositioning of the dressing interface 200 on the cover 125. At least a portion of the shell layer 310 may be configured to extend at least partially through one or more of the plurality of apertures 335 in the contact layer 315. For example, at least a first portion of the shell layer 310 may extend at least partially through the first plurality of apertures 400 in the contact layer 315 (see FIG. 6) and at least a second portion of the shell layer 310 may extend at least partially through the second plurality of apertures 405 in the contact layer 315 (see FIG. 7). In some examples, the diameter D1 of the first plurality of apertures 400 is larger than the diameter D2 of the second plurality of apertures 405, allowing more of the shell layer 310 to come into contact with the cover 125 at each aperture in the first plurality of apertures 400 than is able to come into contact with the cover 125 at each aperture in the second plurality of apertures 405. This results in the two different adhesive regions: the first adhesive region 220; and the second adhesive region 225, wherein the two adhesive regions are on opposite sides of the hinge line 230. The first adhesive region 220 may be formed by a first portion of the contact layer 315 proximate the first plurality of apertures 400 and a first portion of the shell layer 310 extending through the first plurality of apertures 400. The second adhesive region 225 may be formed by a second portion of the contact layer 315 proximate the second plurality of apertures 405 and a second portion of the shell layer 310 extending through the second plurality of apertures 405. The combination of the peel strength of the shell layer 310, the amount of the shell layer 310 extending through the first plurality of apertures 400 and contacting the cover 125, and the peel strength of the contact layer 315 contacting the cover 125 results in a first region peel strength. Likewise, the combination of the peel strength of the shell layer 310, the amount of the shell layer 310 extending through the second plurality of apertures 405 and contacting the cover 125, and the peel strength of the contact layer 315 contacting the cover 125 results in a second region peel strength. The first region peel strength is higher than the second region peel strength. Therefore, the coupling member 205 may have a first region peel strength in the first adhesive region 220 and a second region peel strength in the second adhesive region 225.

The second region peel strength of the second adhesive region 225 may be low enough to permit removal of the second adhesive region 225 from the cover 125 without damage to or destruction of the cover 125. Additionally, in some examples, the first adhesive region 220 may remain attached to the cover 125 when the second adhesive region 225 is removed. The first adhesive region 220 may function as an anchor to hold the dressing interface 200 to the cover 125.

Figure 8:
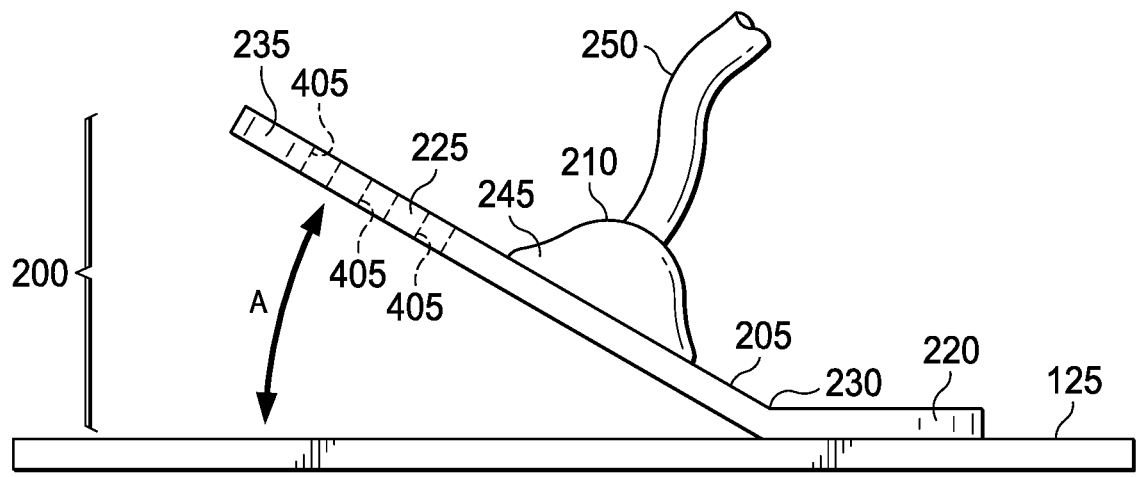
FIG. 8 is a side view of the dressing interface and cover of FIG. 3.

FIG. 8 is a front view of the dressing interface 200 of FIG. 2. The tab 235 may be pulled to remove the second adhesive region 225 from the cover 125. In some embodiments, the tab 235 may be pulled to completely remove the dressing interface 200 from the cover 125. In some embodiments, the tab 235 is non-adhesive so that the tab 235 may be easily lifted up and pulled to remove part or all of the dressing interface 200 from the cover 125. In other embodiments, the tab 235 may include a low-peel-force adhesive that is configured to keep the tab 235 attached to the cover 125 so that the tab 235 is not inadvertently pulled up by being snagged on clothing, medical equipment, other persons, or other objects. Pulling on the tab 235 removes the second adhesive region 225 of the coupling member 205 from the cover 125, causing the second adhesive region 225 to hinge or rotate about hinge line 230 relative to the first adhesive region 220 of the coupling member 205 (as shown by curved line A), with the first adhesive region 220 still adhered to the cover 125. The negative-pressure port 210 may also be located in the second adhesive region 225 and may also hinge or rotate about the hinge line 230. The second plurality of apertures 405 may also hinge or rotate about the hinge line 230. By locating the negative-pressure port 210 in the second adhesive region 225, the bottom side of the negative-pressure port 210 and the interior of the conduit housing 245 can be inspected and/or accessed to remove exudate, clogs, and/or other material from, or otherwise clean, the negative-pressure port 210 and/or the interior of the conduit housing 245. This cleaning can be done without damaging or destroying the cover 125, the tissue interface 120, or the tissue site. Once the negative-pressure port 210 is cleaned, the second adhesive region 225 can be reattached to the cover 125 and negative-pressure therapy can resume.

A number of factors may be utilized to control the first region peel strength and the second region peel strength of the dressing interface 200, including, but not limited to, the area and number of the first plurality of apertures 400 and the second plurality of apertures 405 in the contact layer 315, the thickness of the contact layer 315, the thickness and amount of the adhesive on the shell layer 310, the peel strength of the adhesive on the shell layer 310, and the peel strength of the contact layer 315. An increase in the amount of the adhesive of the shell layer 310 extending through the plurality of apertures 335 generally corresponds to an increase in the peel strength of the dressing interface 200. A decrease in the thickness of the contact layer 315 generally corresponds to an increase in the amount of the adhesive of the shell layer 310 extending through the plurality of apertures 335. Thus, for example, the diameter and configuration of the first plurality of apertures 400 and the second plurality of apertures 405, the amount and peel strength of the adhesive of the shell layer 310, the thickness of the contact layer 315, and the peel strength of the contact layer 315 utilized may be varied to provide a desired first region peel strength and second region peel strength for the dressing interface 200.

Figure 9:
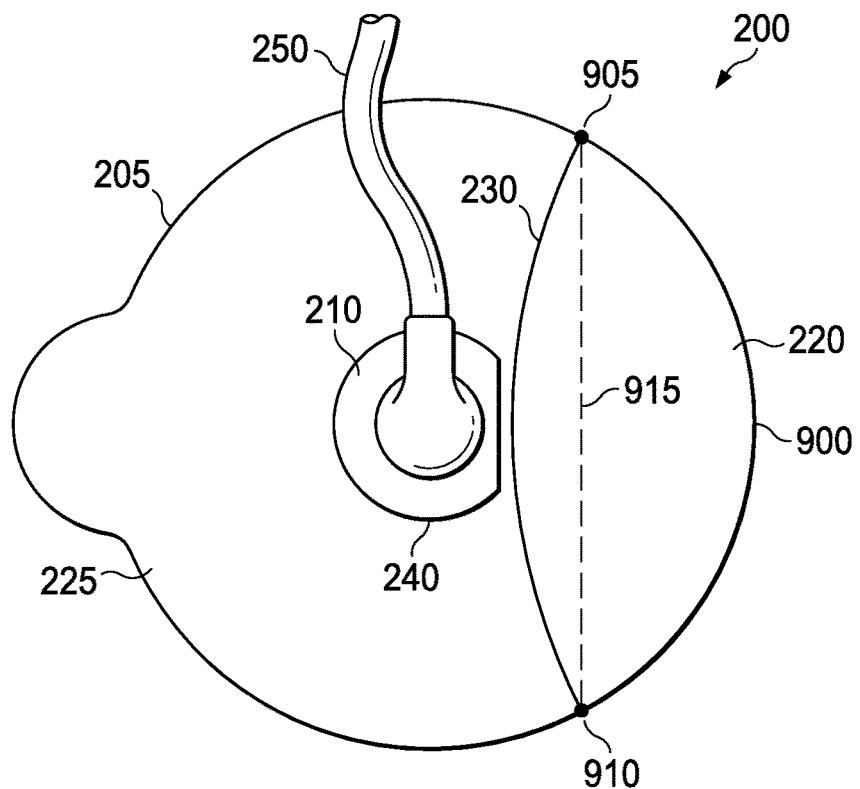
FIG. 9 and FIG. 10 are top views of example configurations of hinge lines that may be associated with some embodiments of the dressing interface of FIG. 2.
Figure 10:
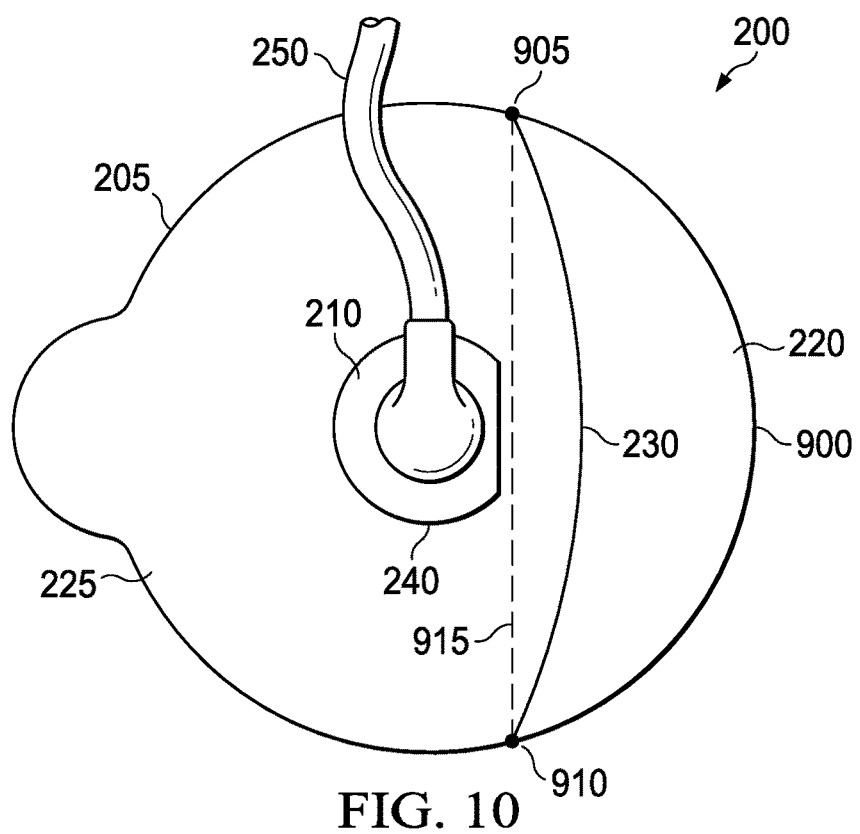

FIG. 9 and FIG. 10 are top views of the dressing interface 200, illustrating additional details that may be associated with certain embodiments. Although the hinge line 230 of various embodiments of the dressing interface 200 is described and illustrated as being straight, in some embodiments the hinge line 230 may be non-linear (e.g., curved, an arc, wavy, sawtooth). In other embodiments, no part of the hinge line 230 intersects the flange 240 of the negative-pressure port 210. In other embodiments, the hinge line 230 may be tangent to the flange 240. In the example embodiment shown in FIG. 9, the hinge line 230 is curved toward the negative-pressure port 210. Coupling member 205 comprises a perimeter 900 and the hinge line 230 has a first end point 905 on the perimeter 900 and a second end point 910 on the perimeter 900. An imaginary line 915 may be drawn from the first end point 905 to the second end point 910, and no part of the imaginary line 915 intersects the flange 240 of the negative-pressure port 210. Accordingly, in the example embodiment shown in FIG. 10, where hinge line 230 is curved away from the negative-pressure port 210, so long as the imaginary line 915 extending from the first end point 905 to the second end point 910 does not intersect the flange 240, the second adhesive region 225 may rotate about the hinge line 230 and a user may be able to easily access the interior of the conduit housing 245 of the negative-pressure port 210.

Figure 11:
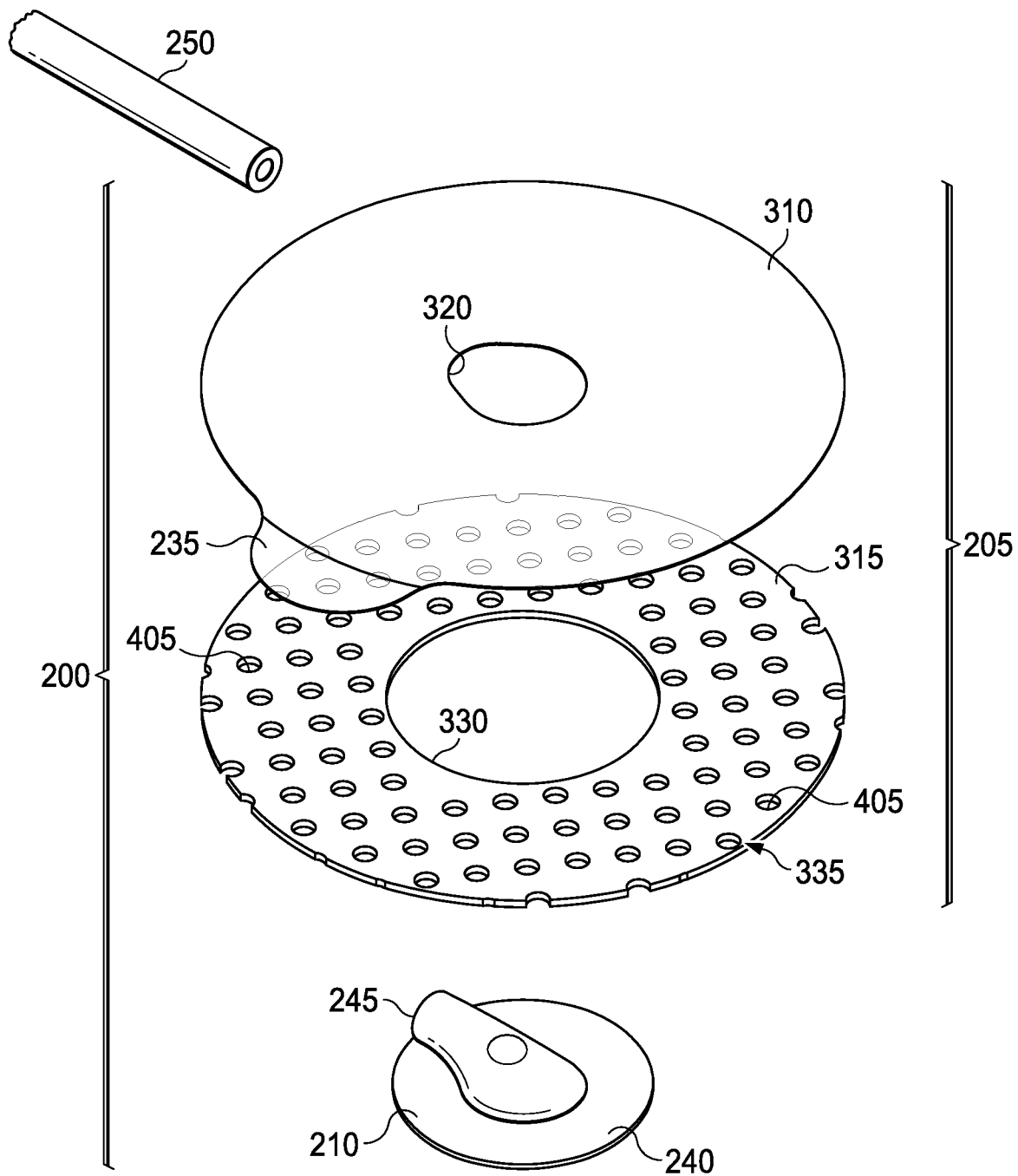
FIG. 11 is an exploded view of another example of a dressing interface, illustrating additional details that may be associated with some example embodiments of the therapy system of FIG. 1.

FIG. 11 is an exploded view of an example configuration of the plurality of apertures 335, illustrating additional details that may be associated with some embodiments of the dressing interface 200. In the example of FIG. 11, the dressing interface 200 includes coupling member 205 configured to be coupled to a negative-pressure port 210. The coupling member 205 may include a shell layer 310, a contact layer 315, and a tab 235. The shell layer 310 may further include an aperture 320 through which the conduit housing 245 of the negative-pressure port 210 is configured to extend. The contact layer 315 has an aperture 330 for receiving the flange 240 of the negative-pressure port 210, and a plurality of apertures 335. As shown in FIG. 11, the flange 240 may be circular and may not include the chord 305 shown in FIGS. 2-5. In some embodiments, flange 240 may include the chord 305. Additionally, the example of the contact layer 315 shown in FIG. 11 only includes a single plurality of apertures 335. In some embodiments, for example, the single plurality of apertures 335 may be the second plurality of apertures 405. Consequently, in some embodiments, the dressing interface 200 may only have a single adhesive region with a single region peel strength. By including only the second plurality of apertures 405, the entirety of the dressing interface 200 may be removed from the cover 125 without damage to or destruction of the cover 125.

Figure 12:
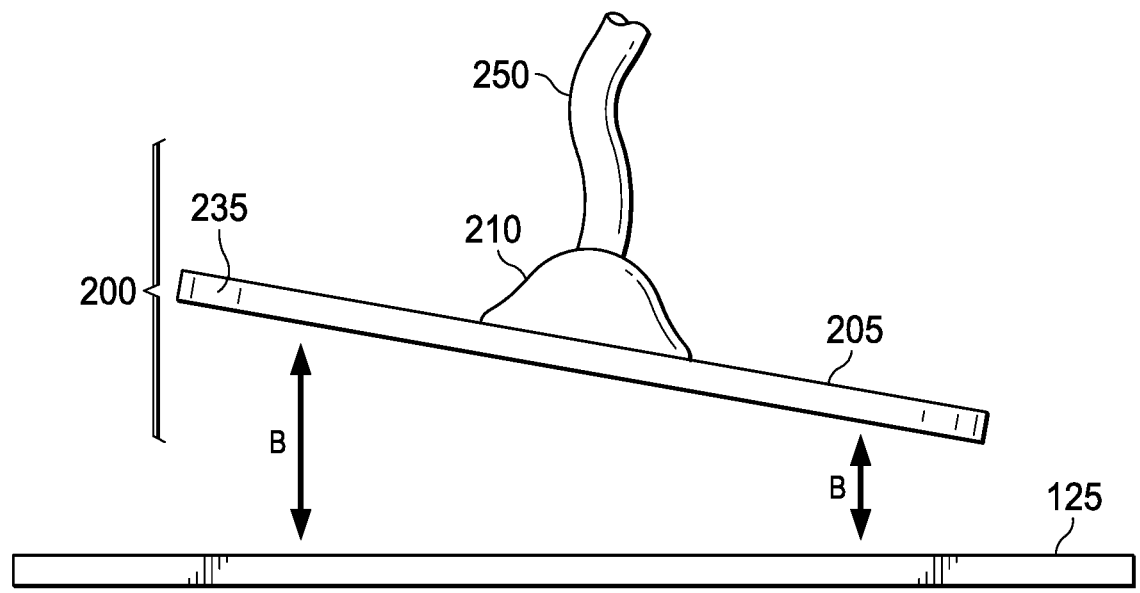
FIG. 12 is a side view of the dressing interface of FIG. 11 and an example of a cover that may be associated with some example embodiments of the therapy system of FIG. 1.

FIG. 12 is a front view of the dressing interface 200 shown in FIG. 11 illustrating the complete removal of the dressing interface 200 from the cover 125 along lines B without damaging or destroying the cover 125 or the tissue interface 120. It will be understood however, that less than the entirety of dressing interface 200 may also be removed from cover 125 without damage to or destruction of the cover 125. The dressing interface 200 may be reattached by pressing down along lines B.

Figure 13:
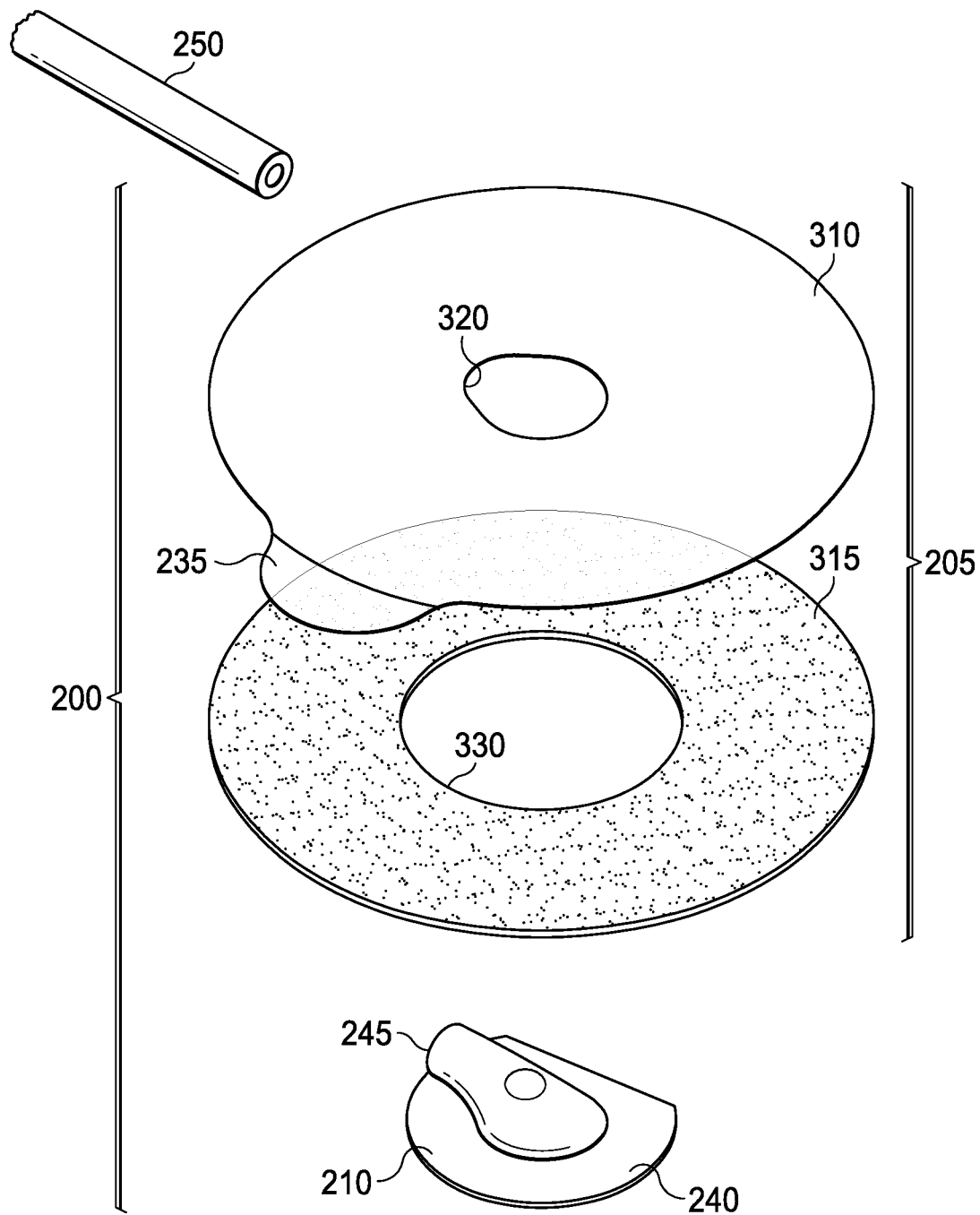
FIG. 13 is an exploded view of another example of a dressing interface, illustrating additional details that may be associated with some example embodiments of the therapy system of FIG. 1.

FIG. 13 is an exploded view of another example configuration of the dressing interface 200, illustrating additional details that may be associated with some embodiments of the dressing interface 200. In the example of FIG. 13, the dressing interface 200 includes coupling member 205 configured to be coupled to a negative-pressure port 210. The coupling member 205 may include a shell layer 310, a contact layer 315, and a tab 235. The shell layer 310 may further include an aperture 320 through which the conduit housing 245 of the negative-pressure port 210 is configured to extend. The contact layer 315 includes an aperture 330 for receiving the flange 240 of the negative-pressure port 210. As shown in FIG. 13, the flange 240 may be circular and may not include the chord 305 shown in FIGS. 2-5. Moreover, unlike the examples of the contact layer 315 shown in FIGS. 2-8 and 11 having a plurality of apertures 335, the example of the contact layer 315 shown in FIG. 13 lacks the plurality of apertures 335. In some embodiments, the dressing interface 200 may only have a single adhesive region with a single region peel strength, wherein the single region peel strength is defined by the peel strength of the contact layer 315. With the low peel strength of the contact layer 315, the entirety of the dressing interface 200 may be removed from the cover 125 without damage to or destruction of the cover 125. In some embodiments, for example, the contact layer 315 has a peel strength in a range of about 0.44 N to about 3.1 N. In some embodiments, for example, the contact layer 315 may comprise or consist essentially of a silicone adhesive having a peel strength of about 2.8 N.

Figure 14:
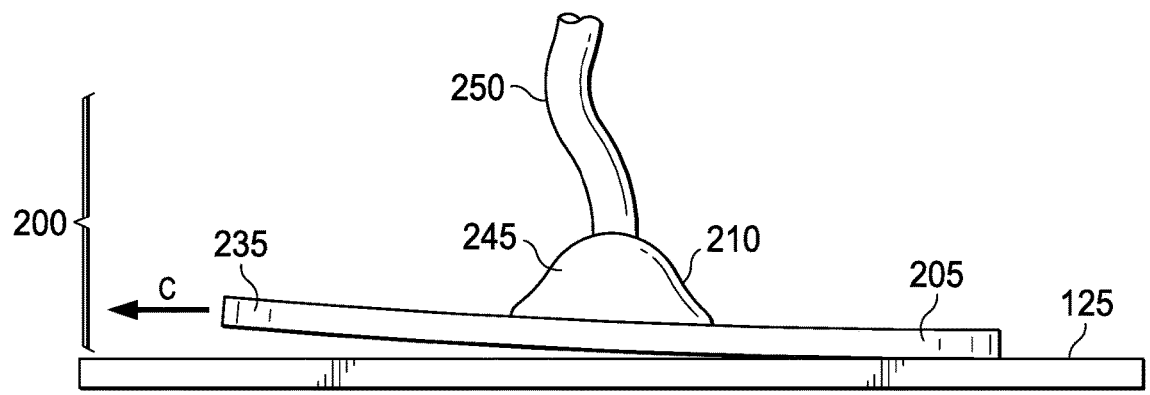
FIG. 14 and FIG. 15 are side views of another example of a dressing interface and a cover, illustrating additional details that may be associated with some example embodiments of the therapy system of FIG. 1.
Figure 15:
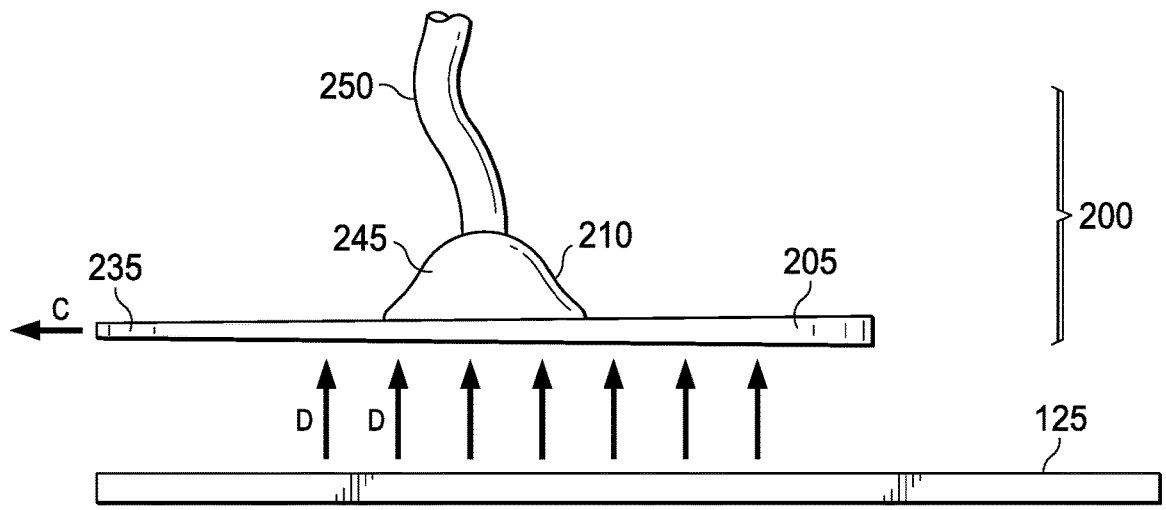

FIG. 14 and FIG. 15 are front views of the dressing interface 200 and the cover 125 illustrating additional details that may be associated with some embodiments of the dressing interface 200. In the example of FIG. 14 and FIG. 15, the coupling layer 205 of the dressing interface 200 may comprise a stretch-releasing adhesive. In some examples, the stretch-releasing adhesive may be COMMAND brand adhesives commercially available from 3M Company of Minneapolis, Minnesota. The tab 235 of the coupling layer 205 may be pulled along line C in a direction substantially parallel to the coupling layer 205 to remove dressing interface 200 from cover 125. As tab 235 is pulled along line C, the stretch-releasing adhesive of the coupling layer 305 is stretched and thins which reduces the peel force of the stretch-releasing adhesive until such point that the coupling layer 305 lifts away from cover 125 as shown by lines D. In some embodiments, the coupling layer 305 may be perforated or cut along hinge line 230 such that when tab 235 is pulled, the perforations may be broken and the portion of the coupling layer 305 on the tab 235 side of the hinge line 230 may be removed, leaving the portion of the coupling layer 305 on the opposite side of the hinge line 230 intact and attached to cover 125. In such embodiments, a new stretch-releasing adhesive portion may be provided and the dressing interface 200 may be reapplied to the cover 125. In some embodiments, the coupling layer 305 may be perforated or cut along the hinge line 230 and may include a tab 235 on each side of the hinge line 230 such that each side of the coupling layer 305 may be independently removable. In other embodiments, the contact layer 315 may comprise a stretch-releasing adhesive which can be independently removed from shell layer 310. After contact layer 315 is stretched to remove contact layer 315 from the cover 125 and the shell layer 310, a new contact layer 315 may be applied to the shell layer 310 and the dressing interface 200 may be reapplied.

Figure 16:
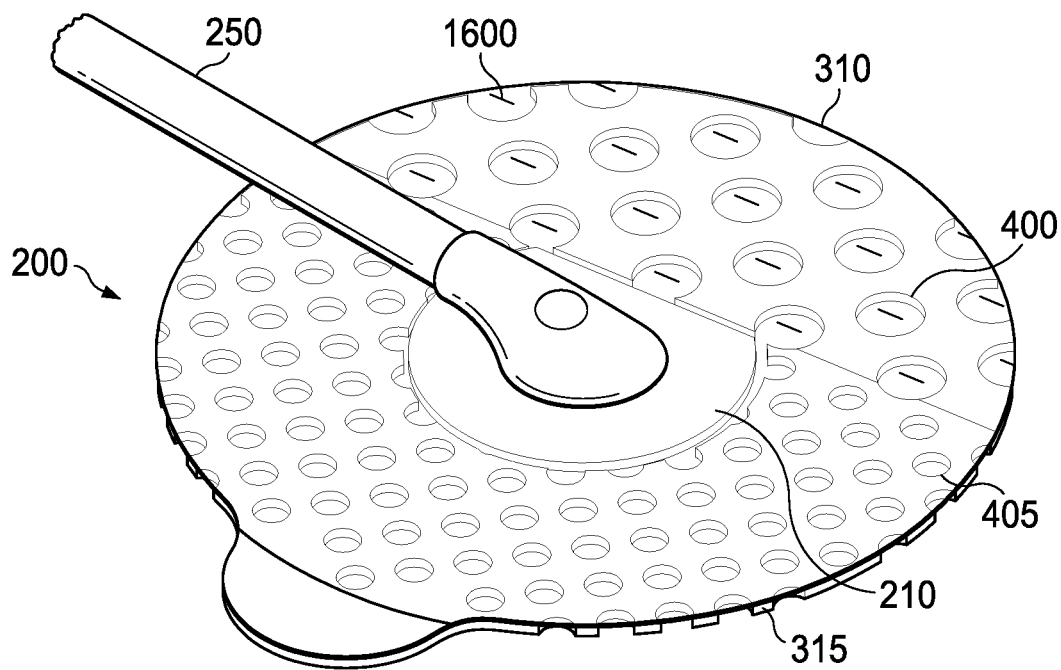
FIG. 16 is an isometric view of another example of a dressing interface, illustrating additional details that may be associated with some example embodiments of the therapy system of FIG. 1.

FIG. 16 is an isometric view of another example configuration of the dressing interface 200, illustrating additional details that may be associated with some embodiments of the dressing interface 200. In the example of FIG. 15, the dressing interface 200 includes a plurality of perforations 1600 in the shell layer 310 aligned with at least a portion of the first plurality of apertures 400. Over time, in the first adhesive region 220, the bond of the dressing interface 200 to the cover 125 may increase, and thus the first adhesive region may offer higher resistance to removal. Additionally, the application of heat can increase the bond strength of the adhesive of the shell layer 310. Accordingly, the perforations 1600 may be configured to permit a liquid to be drawn through the plurality of perforations 1600 such that the liquid contacts the adhesive of the shell layer 310. The liquid then interacts with the adhesive of the shell layer 310 to reduce the peel strength of the adhesive of the shell layer 310. This allows the first adhesive region 220 to be removed from the cover 125 without damage to or destruction of the cover 125, even if the dressing interface 200 has been adhered to the cover 125 for a long period of time. In some embodiments, the liquid may be an alcohol, such as isopropyl alcohol. For example, a user may apply a small amount of isopropyl alcohol via a readily available alcohol wipe to the shell layer 310. The isopropyl alcohol is then drawn through the plurality of perforations 1600 and will soften the adhesive of the shell layer 310 over about a 2 to 3 minute period, thus reducing the peel strength of the adhesive of the shell layer 310. The dressing interface 200 may then be removed from the cover 125. After removal, the isopropyl alcohol will evaporate, and the peel strength of the adhesive of the shell layer 310 will return to only slightly less than its original level (about 80%), allowing the dressing interface 200 to be re-adhered to the cover 125. In some embodiments, the plurality of perforations 1600 may comprise slits, slots, fenestrations, or other apertures which permit the flow of liquid from above the shell layer 310 to the adhesive of the shell layer 310. The plurality of perforations 1600 do not adversely affect the seal or integrity of the tissue site as the location of the plurality of perforations 1600 in the first adhesive region is a sufficient distance away from pneumatic or fluid connection with the tissue site.

Figure 17:
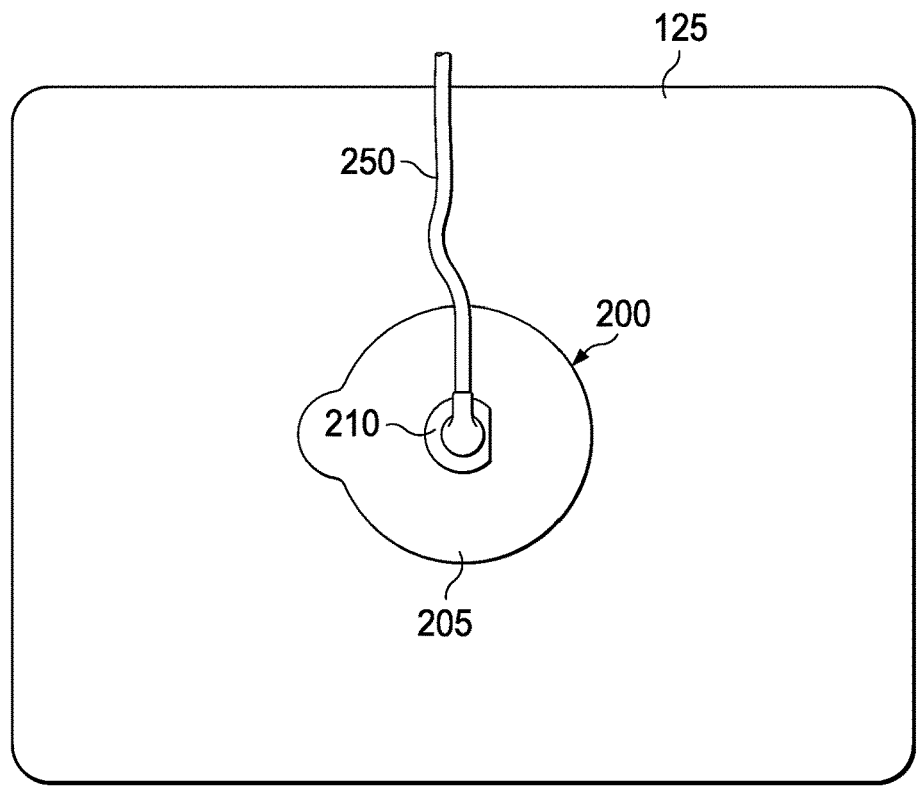
FIG. 17 and FIG. 18 are top views of another example of a dressing interface and a cover, illustrating additional details that may be associated with some example embodiments of the therapy system of FIG. 1.
Figure 18:
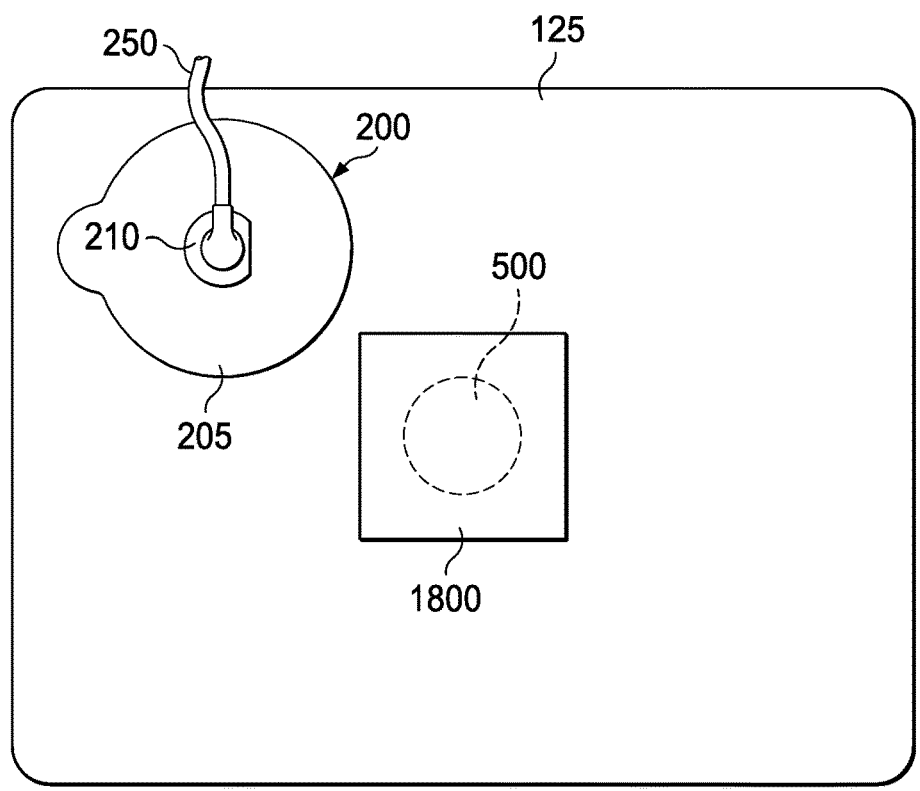

FIG. 17 and FIG. 18 are top views of the dressing interface 200 and the cover 125 illustrating in greater detail the ability to move the dressing interface 200. As shown in the example of FIG. 17, the dressing interface 200 is at an initial position on the cover 125. If the dressing interface 200 needs to be moved for a particular reason, the dressing interface 200 can be removed and placed in a second location as shown in FIG. 18. This can be accomplished without removal of the cover 125 and underlying tissue interface 120 from the tissue site of the patient. A new aperture may be cut through the cover 125 and the dressing interface 200 may be sealed over the new aperture to fluidly couple fluid conductor 250 to the aperture. As shown in FIG. 18, the aperture 500 in the cover 125 may be sealed by a patch 1800. The patch 1800 may be the same material as the cover 125. With the dressing interface 200 located at the second location on the cover 125 and the aperture 500 sealed, negative-pressure therapy can be resumed.

Figure 19:
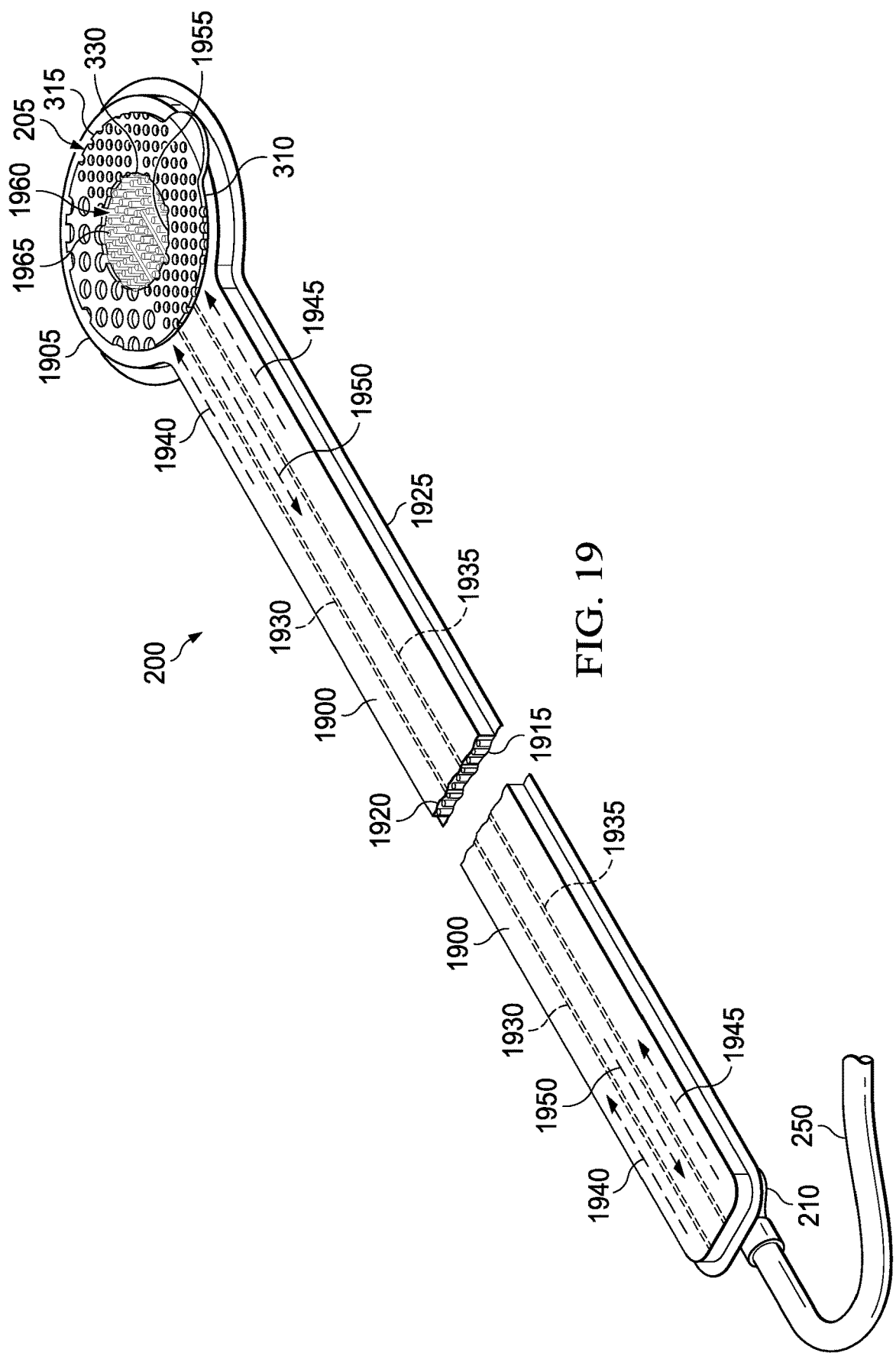
FIG. 19 is a bottom segmented isometric view of a dressing interface illustrating additional details that may be associated with some example embodiments of the therapy system of FIG. 1.

FIG. 19 is a bottom segmented isometric view of another example configuration of the dressing interface 200, illustrating additional details that may be associated with some embodiments. As shown in FIG. 19, in some embodiments, the dressing interface 200 may include a bridge 1900, which generally may have a low-profile structure. The bridge 1900 may be configured to fluidly couple the negative-pressure source 105 to the therapeutic environment of the dressing 110. The bridge 1900 of FIG. 19 is substantially flat and flexible, and may also be compressible without occluding or blocking the fluid pathway between the fluid conductor 250 and the tissue interface 120. In some embodiments, the dressing interface 200 may comprise an applicator 1905, which can be adapted to be positioned in fluid communication with the tissue interface 120. The bridge 1900 can be fluidly coupled to the applicator 1905 and extend to the negative-pressure port 210. The bridge 1900 may have a substantially flat profile, and the negative-pressure port 210 may be configured to fluidly couple the bridge 1900 to a tube or other round fluid conductor, such as the fluid conductor 250. In some embodiments, the dressing interface 200 of FIG. 19 may have a length that can range from about 15 cm to about 30 cm. In some embodiments, the bridge 1900 and the applicator 1905 may be formed as a single device as shown. In other embodiments, the bridge 1900 and the applicator 1905 may be separate components that are coupled together to form a single device. In yet other embodiments, the bridge 1900 and the applicator 1905 may be separate components that may be used independently of each other as a single component in the therapy system 100.

As further shown in FIG. 19, the applicator 1905 may be bulbous, circular, or any shape suitable for applying therapy to the tissue interface 120, depending on the size and nature of the tissue site. The bridge 1900 in the example of FIG. 19 is generally long and narrow. In some example embodiments, the bridge 1900 and the applicator 1905 may comprise a top layer, such as a first layer 1915, and a base layer, such as a second layer 1920. The second layer 1920 may be coupled to the first layer 1915 around the periphery of the first layer 1915 to form an enclosed space within the dressing interface 200. The enclosed space may be formed between the first layer 1915 and the second layer 1920 of both the bridge 1900 and the applicator 1905. In some embodiments, the enclosed space may be sealed along the periphery of the bridge 1900, the applicator 1905, or both. The first layer 1915 and the second layer 1920 may both be formed from or include a polymeric film. The first layer 1915 and the second layer 1920 may be coupled around the periphery of the dressing interface 200 to form the enclosed space by welding (RF or ultrasonic), heat sealing, or adhesive bonding such as, for example, acrylics or cured adhesives. For example, the first layer 1915 and the second layer 1920 may be welded together around the periphery of the dressing interface 200 and may form a flange 1925 around the periphery of the dressing interface 200 as a result of the weld. One skilled in the art would understand that there are a variety of methods for coupling the first layer 1915 and the second layer 1920 to form the enclosed space within the dressing interface 200.

The bridge 1900 of FIG. 19 may further comprise at least one barrier or wall, such as a first wall 1930, between the first layer 1915 and the second layer 1920. In some embodiments, the first wall 1930 may extend from the end of the bridge 1900 adjacent the negative-pressure port 210 into the applicator 1905 to form at least two enclosed spaces or fluid pathways between the first layer 1915 and the second layer 1920 within the dressing interface 200. In some examples, the dressing interface 200 may further comprise a second barrier, such as a second wall 1935, between the first layer 1915 and the second layer 1920. In some embodiments, the second wall 1935 also may extend from the end of the bridge 1900 adjacent the negative-pressure port 210 into the applicator 1905. In some example embodiments, the first wall 1930 and the second wall 1935 may comprise a polymeric film coupled between the first layer 1915 and the second layer 1920. In some other example embodiments, the first wall 1930 and the second wall 1935 may comprise a weld (RF or ultrasonic), a heat seal, an adhesive bond, or a combination of any of the foregoing. In those embodiments comprising two walls, e.g., the first wall 1930 and the second wall 1935, such embodiments may form three enclosed spaces or fluid pathways within the enclosed space between the first layer 1915 and the second layer 1920. In some embodiments, two of the fluid pathways may be dedicated to measuring pressure. For example, a first pressure-sensing pathway 1940 and a second pressure-sensing pathway 1945 (as indicated by the dashed line arrows) in the example of FIG. 19 may be configured as feedback pathways. A third fluid pathway, such as a negative-pressure pathway 1950 (as indicated by the dashed line arrows), may be utilized for providing negative pressure.

In some example embodiments, the first pressure-sensing pathway 1940, the negative-pressure pathway 1950, and the second pressure-sensing pathway 1945 may be fluidly coupled to the fluid conductor 250 by the negative-pressure port 210. For example, the negative-pressure pathway 1950 may be fluidly coupled to the fluid conductor 250 so that the negative-pressure pathway 1950 functions to deliver negative pressure to the tissue interface 120. The first pressure-sensing pathway 1940 and the second pressure-sensing pathway 1945 may be fluidly coupled to the fluid conductor 250. In other embodiments, the first pressure-sensing pathway 1940 and the second pressure-sensing pathway 1945 both may be fluidly coupled to a single space within the negative-pressure port 210 that is also fluidly coupled to the fluid conductor 250. In some example embodiments, the other end of the first pressure-sensing pathway 1940, the negative-pressure pathway 1950, and the second pressure-sensing pathway 1945 may terminate within the applicator 1905 and may be fluidly coupled to each other within the applicator 1905 for delivering and sensing the negative pressure associated with the tissue interface 120.

The applicator 1905 may comprise an opening or aperture 1955 in the second layer 1920, adapted to fluidly couple the enclosed space of the dressing interface 200 to the tissue interface 120. The aperture 1955, along with the first layer 1915 and the second layer 1920 portions of the applicator 1905 may define a recessed space 1960 within the enclosed space of the applicator 1905, wherein the recessed space 1960 is adapted to be in fluid communication with the tissue interface 120 in use. The portion of the recessed space 1960 covered by the second layer 1920 of the applicator 1905 may be referred to as a covered space. In some embodiments, the first wall 1930 and the second wall 1935 may extend only partially into the recessed space 1960 so that the end of the first wall 1930 and the second wall 1935 are exposed by the aperture 1955. The first pressure-sensing pathway 1940 and the second pressure-sensing pathway 1945 may be in fluid communication with the recessed space 1960. The negative-pressure pathway 1950 may also be in fluid communication with the recessed space 1960 and can be adapted to deliver negative pressure to the tissue interface 120 through the recessed space 1960. In some example embodiments (not shown), the first wall 1930 and the second wall 1935 may extend beyond the aperture 1955 so that less of the first pressure-sensing pathway 1940 and the second pressure-sensing pathway 1945 are being exposed to negative pressure being delivered to the tissue interface 120 by the negative-pressure pathway 1950 to avoid occlusions and/or blockages from the tissue site.

The dressing interface 200 may further comprise a means for supporting fluid paths under pressure. In some embodiments, the means of support may comprise a plurality of support features, such as flexible projections, standoffs, nodes, cells porous textile, porous foam, or some combination of features disposed in a fluid path. For example, the dressing interface 200 of FIG. 19 comprises a plurality of supports 1965. The supports 1965 in FIG. 19 may be generally characterized as bubbles that have a bottom portion extending from the first layer 1915 and a top portion extending within the enclosed spaces toward the second layer 1920 outside the recessed space 1960. Within the recessed space 1960, the top portion of the supports 1965 extending from the first layer 1915 may extend toward the tissue interface 120 and may be adapted to come in direct contact with the tissue interface 120 in use, or may be positioned above the tissue interface 120. Features such as the supports 1965 can provide a cushion to help prevent the enclosed spaces of the dressing interface 200 from collapsing as a result of external forces. In some example embodiments, the top portion of the supports 1965 may come in contact with the second layer 1920, and in some other example embodiments, the top portion of the supports 1965 may be coupled to the second layer 1920.

As further shown in FIG. 19, in some embodiments, the dressing interface 200 may further include the coupling member 205 for releasably coupling the applicator 1905 to the dressing 110. The shell layer 310 of the coupling member 205 may be coupled with the dressing interface 200, such that the shell layer 310 is located between the contact layer 315 and the second layer 1920 of the dressing interface 200. The coupling member 205 may be located on the applicator 1905 with the aperture 330 of the coupling member 205 configured to be in fluid communication with the aperture 1955. In some embodiments, the aperture 330 may be congruent with the aperture 1955. In some embodiments, in addition to the first side of the shell layer 310 comprising an adhesive as described above, the second side of the shell layer 310 may also comprise an adhesive so that the shell layer 310 may be coupled to second layer 1920 of the dressing interface 200. In some embodiments, an adhesive may be applied to the second layer 1920 of the dressing interface 200 to couple the shell layer 310 to the dressing interface 200.

In some embodiments, the shell layer 310 may be omitted from the coupling member 205 and an adhesive may be coated or deposited on the second layer 1920 of the dressing interface 200. In such embodiments, the second layer 1920 of the dressing interface 200 may serve as the shell layer 310. The adhesive may be a medically-acceptable adhesive. The adhesive may also be flowable. For example, the adhesive may comprise an acrylic adhesive, rubber adhesive, high-tack or tacky silicone adhesive, polyurethane, or other adhesive substance. In some embodiments, the adhesive of the second layer 1920 may be a pressure-sensitive adhesive, such as an acrylic adhesive with coating weight of 15 grams/m$^2$ (gsm) to 70 grams/m$^2$ (gsm). In some embodiments, the adhesive may have a peel strength or resistance to being peeled from a stainless steel material in a range of about 6.4N to about 8.8 N. In some embodiments, the adhesive may have a peel strength or resistance to being peeled from a stainless steel material of about 7.8 N. In some embodiments, the adhesive of the second layer 1920 may be reduced or deactivated using ultraviolet light. Ultraviolet light may be shined upon the dressing interface 200 and the ultraviolet light may reduce the peel strength of the adhesive a sufficient amount to allow removal of the dressing interface 200 from the cover 125 without damage to or destruction of the cover 125.

Figure 20:
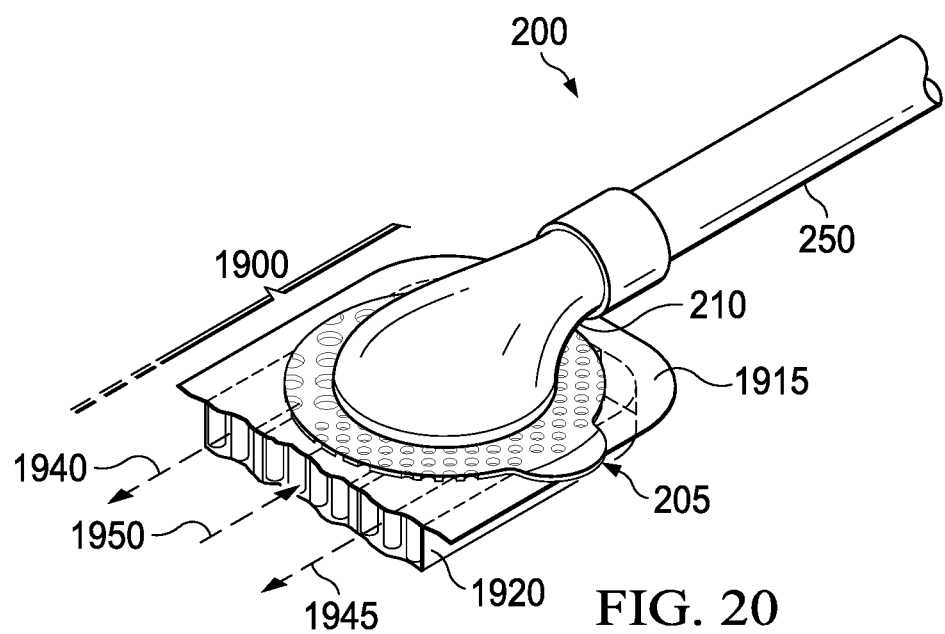
FIG. 20 is a segmented isometric view of the top of the dressing interface of FIG. 19 that may be associated with some example embodiments of the therapy system 100 of FIG. 1.

FIG. 20 is a segmented isometric view of the top of the dressing interface 200 of FIG. 19 that may be associated with some example embodiments of the therapy system 100 of FIG. 1. As shown in FIG. 20, in some embodiments, the coupling member 205 may be configured for releasably coupling the negative-pressure port 210 to the bridge 1900. The coupling member 205 may be used to couple the negative-pressure port 210 to the first layer 1915. In some embodiments, the dressing interface 200 includes a first coupling member 205 on the applicator 1905 and a second coupling member 205 on the bridge 1900. In some embodiments, the dressing interface 200 includes the coupling member 205 on the applicator 1905 but not the bridge 1900. In some embodiments, the dressing interface 200 includes the coupling member 205 on the bridge 1900 but not the applicator 1905.

While the plurality of apertures 335 are illustrated as circular, in other embodiments, the plurality of apertures 335 may comprise elongated apertures, such as slots, partially located in the first adhesive region 220 and extending across the hinge line 230 into the second adhesive region 225. The portion of the elongated aperture in the first adhesive region 220 may have a greater open area than the portion of the elongated aperture in the second adhesive region 225. In some embodiments, for example, the elongated apertures may have a wider open portion in the first adhesive region 220 and a narrower open portion in the second adhesive region 225.

Therefore, a method of treating a tissue site with negative pressure may be carried out utilizing the dressing interface 200. The method may comprise applying the tissue interface 120 to the tissue site, applying a cover 125 on a patient's epidermis to form a fluid seal over the tissue interface 120, coupling the dressing interface 200 to first location on the cover 125, fluidly coupling the tissue interface 120 to a negative-pressure source 105, and applying negative pressure from the negative-pressure source 105 to the tissue interface 120 and promoting healing and tissue granulation. In some embodiments, the method may further include removing at least a portion of the dressing interface 200 from the cover 125 and then reapplying the dressing interface 200 to the cover 125. In some embodiments, the method may further include cleaning or removing a blockage from the dressing interface 200 after removing at least a portion of the dressing interface 200 from the cover 125 and before reapplying the dressing interface 200 to the cover 125. In some embodiments, the method may further include removing the entirety of the dressing interface 200 from the cover 125 and reapplying the dressing interface 200 to the cover 125. In some embodiments, the method may further include reapplying the dressing interface 200 to a second location on the cover 125, wherein the second location is different from the first location. In some embodiments, the method may further include cleaning or removing a blockage from the dressing interface 200 after removing the entirety of the dressing interface 200 from the cover 125 and before reapplying the dressing interface 200 to the cover 125.

The systems, apparatuses, and methods described herein may provide significant advantages. For example, the dressing interface 200 can be removed, replaced, or relocated to resolve connection issues quickly and efficiently without damaging or destroying the cover 125. The ability to reposition the negative-pressure port 210 on the cover 125 using the dressing interface 200 can reduce troubleshooting time and may avoid an entire change of the dressing 110. The dressing interface 200 may also avoid a complete replacement of the negative-pressure port 210, the tissue interface 120, and/or the cover 125, reducing the costs of an entirely new dressing 110. As a result, therapy disruptions from removal of an entire dressing 110 may be reduced.

The systems, apparatuses, and methods described herein may provide yet additional significant advantages. For example, if the negative-pressure port 210 becomes clogged, the dressing interface 200 may be easily peeled or lifted up and the negative-pressure port 210 may be cleaned. Additionally, topical medications may be easier to apply while the negative-pressure port 210 is peeled up. Following cleaning and/or the application of medication, the second adhesive region 225 of the dressing interface 200 can then be pressed back onto the cover 125 to reseal the negative-pressure port 210 to the cover and therapy can resume, all without damage to or destruction of the cover 125. Additionally, in some embodiments, the entire dressing interface 200 may be removed and relocated without damage to or destruction of the cover 125. Changing the position of the negative-pressure port 210 on the cover 125 may be required under certain circumstances when, following the initial placement, there is a more appropriate location on the dressing 110 that may accommodate more fluid using positional gravity. Additionally, the dressing interface 200 and the negative-pressure port 210 can withstand some tugging or pulling force without damaging or destroying the cover 125. The dressing interface 200 may also avoid the need to completely replace the negative-pressure port 210 if a leak occurs. Namely, if a leak occurs, the dressing interface 200 can be peeled or lifted up and placed back down onto the cover 125 to reseal the negative-pressure port 210 to the cover 125.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing interface for connecting a negative-pressure source to a dressing, the dressing interface comprising:
    a coupling member configured to be coupled to a cover of the dressing, the coupling member comprising:
        a contact layer comprising a first aperture;
        a shell layer coupled to the contact layer and configured to be opposite the cover, the shell layer having a second aperture;
        a first adhesive region having a first region peel strength;
        a second adhesive region having a second region peel strength less than the first region peel strength;
        a hinge line between the first adhesive region and the second adhesive region, with the first adhesive region located on a first side of the hinge line and the second adhesive region on a second side of the hinge line, the second side opposite the first side; and
        an aperture formed by the first aperture and the second aperture, the aperture located in the second adhesive region on the second side of the hinge line; and
    a negative-pressure port for the delivery of negative pressure, the negative-pressure port comprising:
        a flange coupled to the shell layer located in the first aperture of the contact layer; and
        a conduit housing coupled to the flange and extending through the second aperture in the shell layer.

2. The dressing interface of claim 1, wherein
    the contact layer comprises a plurality of apertures; and
    wherein the shell layer is configured to extend at least partially through the plurality of apertures in the contact layer.

3. The dressing interface of claim 2, wherein at least one of the plurality of apertures is located in the first adhesive region and extends across the hinge line into the second adhesive region.

4. The dressing interface of claim 2, wherein the plurality of apertures further comprises:
    a first plurality of apertures; and
    a second plurality of apertures.

5. The dressing interface of claim 4, wherein the shell layer is configured to extend at least partially through the first plurality of apertures to form the first adhesive region, and the shell layer is configured to extend at least partially through the second plurality of apertures to form the second adhesive region.

6. The dressing interface of claim 4, wherein:
    the first adhesive region is configured to be formed by a first portion of the contact layer proximate the first plurality of apertures and a first portion of the shell layer extending through the first plurality of apertures; and
    the second adhesive region is configured to be formed by a second portion of the contact layer proximate the second plurality of apertures and a second portion of the shell layer extending through the second plurality of apertures.

7. The dressing interface of claim 4, wherein each aperture of the first plurality of apertures has a first open area, and each aperture of the second plurality of apertures has a second open area, and the second open area is less than the first open area.

8. The dressing interface of claim 2, wherein the contact layer comprises one or more of a silicone adhesive, a hydrocolloid adhesive, and a polyurethane gel adhesive.

9. The dressing interface of claim 2, wherein the shell layer comprises one or more of an acrylic adhesive, a tacky silicone adhesive, and a pressure-sensitive adhesive.

10. The dressing interface of claim 1, wherein no part of the hinge line intersects the aperture.

11. The dressing interface of claim 1, wherein the negative-pressure port and the second adhesive region are configured to rotate around the hinge line.

12. The dressing interface of claim 1, wherein the flange has a circular shape truncated by a chord, forming a truncated circle, the chord configured to be parallel to the hinge line.

13. The dressing interface of claim 1, wherein the second adhesive region is configured to be removable from the cover without destruction of the cover, while the first adhesive region is configured to remain adhered to the cover.

14. The dressing interface of claim 1, wherein the contact layer further comprises a first tab on the second side of the hinge line and the shell layer comprises a second tab on the second side of the hinge line, the first tab and the second tab cooperating to form a tab of the coupling member.

\* \* \* \* \*